(12) United States Patent
Jäger et al.

(10) Patent No.: US 10,907,128 B2
(45) Date of Patent: Feb. 2, 2021

(54) CELL CULTURING SYSTEM FOR CULTURING ADHERENT CELLS AND LIQUID SUPPLY INTERFACE COMPRISING A CELL CULTURE CONTAINER

(71) Applicant: Hamilton Bonaduz AG, Bonaduz (CH)

(72) Inventors: Thomas Jäger, Bonaduz (CH); Dirk Schlenker, Stuttgart (DE); Nabih Othman, Musberg (DE); Oliver Kühne, Malans (CH)

(73) Assignee: Hamilton Bonaduz AG, Bonaduz (CH)

( * ) Notice: Subject to any disclaimer, the term of this patent is extended or adjusted under 35 U.S.C. 154(b) by 18 days.

(21) Appl. No.: 16/119,002

(22) Filed: Aug. 31, 2018

(65) Prior Publication Data

US 2018/0371398 A1 Dec. 27, 2018

Related U.S. Application Data

(62) Division of application No. 14/762,653, filed as application No. PCT/EP2014/051072 on Jan. 21, 2014, now Pat. No. 10,093,893.

(30) Foreign Application Priority Data

Jan. 23, 2013 (DE) .......................... 10 2013 201 069

(51) Int. Cl.
*C12M 1/00* (2006.01)
*C12M 1/26* (2006.01)
(Continued)

(52) U.S. Cl.
CPC ............ *C12M 41/44* (2013.01); *C12M 23/40* (2013.01); *C12M 29/00* (2013.01); *C12M 33/07* (2013.01);
(Continued)

(58) Field of Classification Search
CPC ...................................................... C12M 41/44
(Continued)

(56) References Cited

U.S. PATENT DOCUMENTS 2,366,412 A * 1/1945 Lambert ............. F16K 31/0631
251/129.1
3,893,887 A 7/1975 Smith et al.
(Continued)

FOREIGN PATENT DOCUMENTS

CN 1446924 10/2003
DE 3508151 9/1986
(Continued)

OTHER PUBLICATIONS

International Search Report of PCT/EP2014/051072 dated Jun. 18, 2014, 6 pages.
(Continued)

*Primary Examiner* — Holly Kipouros
(74) *Attorney, Agent, or Firm* — Rankin, Hill & Clark LLP

(57) ABSTRACT

The invention relates to a liquid supply interface for a cell culture system for supplying cell cultures found in different cell culture containers with a nutrient medium, wherein the liquid supply interface comprises: a housing defining a flow area; a first connection formation for the liquid-transferring connection of a first fluid line to the housing; a second connection formation formed separately from the first for the liquid-transferring connection of a second fluid line to the housing; a third connection formation formed separately from the first two for the liquid-transferring connection of the housing to a third fluid line; a coupling formation formed separately from the connection formations, which is formed for the producible and detachable liquid-transferring cou-
(Continued)

pling contact according to the operation, with a corresponding counter-coupling formation of a cell culture container.

5 Claims, 21 Drawing Sheets

(51) Int. Cl.
    *F16K 31/02*     (2006.01)
    *C12M 1/34*     (2006.01)
    *C12M 1/12*     (2006.01)

(52) U.S. Cl.
    CPC ............ *C12M 37/04* (2013.01); *C12M 39/00* (2013.01); *C12M 41/00* (2013.01)

(58) Field of Classification Search
    USPC ...................................................... 435/289.1
    See application file for complete search history.

(56) References Cited

U.S. PATENT DOCUMENTS

| | | | |
|---|---|---|---|
| 4,826,002 A | | 5/1989 | Matuura |
| 5,424,209 A | | 6/1995 | Kearney |
| 5,565,353 A | | 10/1996 | Klebe et al. |
| 5,994,129 A | | 11/1999 | Armstrong et al. |
| 2004/0029264 A1 | * | 2/2004 | Robbins, Jr. ............ C12M 27/12 435/291.6 |
| 2011/0223076 A1 | | 9/2011 | Wynn |
| 2013/0064738 A1 | * | 3/2013 | Berger .................... B01J 4/008 422/521 |
| 2014/0087455 A1 | | 3/2014 | Kobayashi et al. |

FOREIGN PATENT DOCUMENTS

| | | |
|---|---|---|
| DE | 4207346 | 9/1993 |
| DE | 10011866 | 9/2001 |
| DE | 102004023053 | 12/2005 |
| DE | 102006001623 | 7/2007 |
| DE | 602004010474 | 11/2008 |
| DE | 60224951 | 1/2009 |
| DE | 102008023545 | 11/2009 |
| DE | 102008035644 | 2/2010 |
| JP | S63-503201 | 11/1988 |
| JP | 2005-198626 | 7/2005 |
| JP | 2007-222064 | 9/2007 |
| WO | 1996016161 | 5/1996 |
| WO | 2003076599 | 9/2003 |
| WO | 2004106484 | 12/2004 |
| WO | 2010068280 | 6/2010 |
| WO | 2011090781 | 7/2011 |
| WO | 20120141055 | 10/2012 |

OTHER PUBLICATIONS

International Preliminary Report on Patentability of PCT/EP2014/051072 dated Jul. 28, 2015, 16 pages.
German Search Report of Application No. DE 10 2013 201 069.9 dated Jan. 14, 2014, 5 pages.
Office Action of Application No. CN 201480005742.1 dated Jun. 22, 2016, 16 pages (English and Chinese).
Office Action of U.S. Appl. No. 16/118,922 dated Aug. 28, 2020, 14 pages.

* cited by examiner

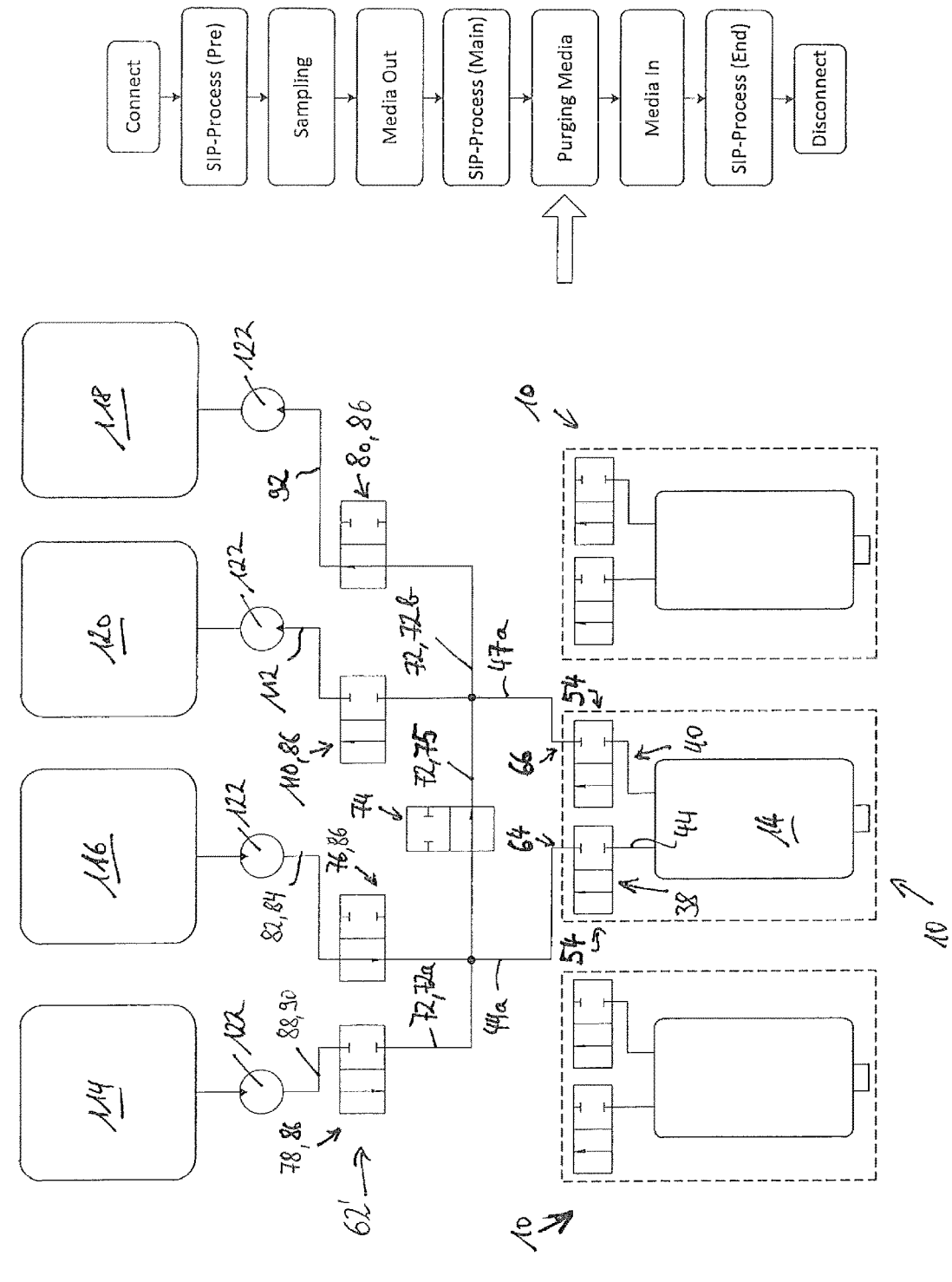

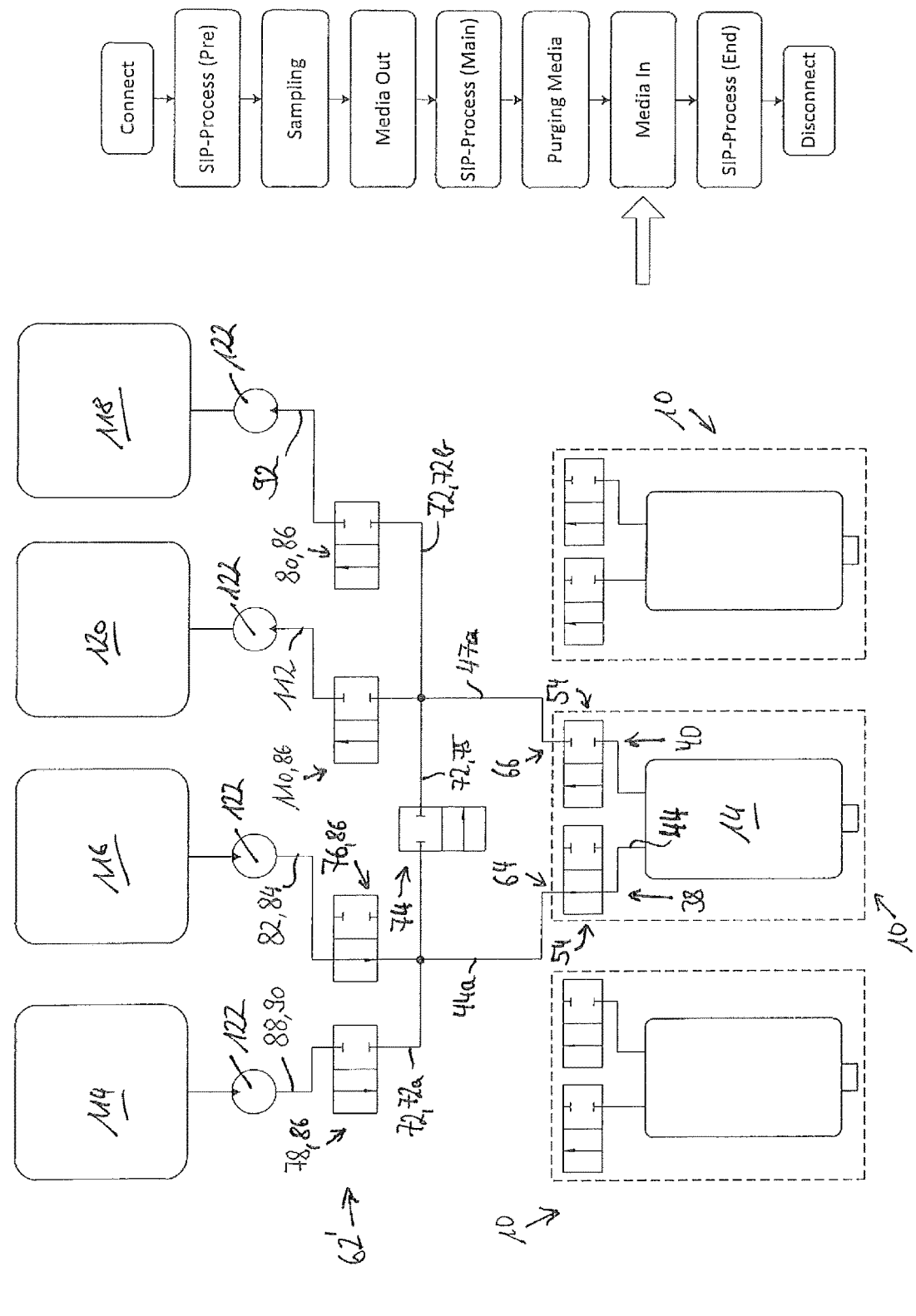

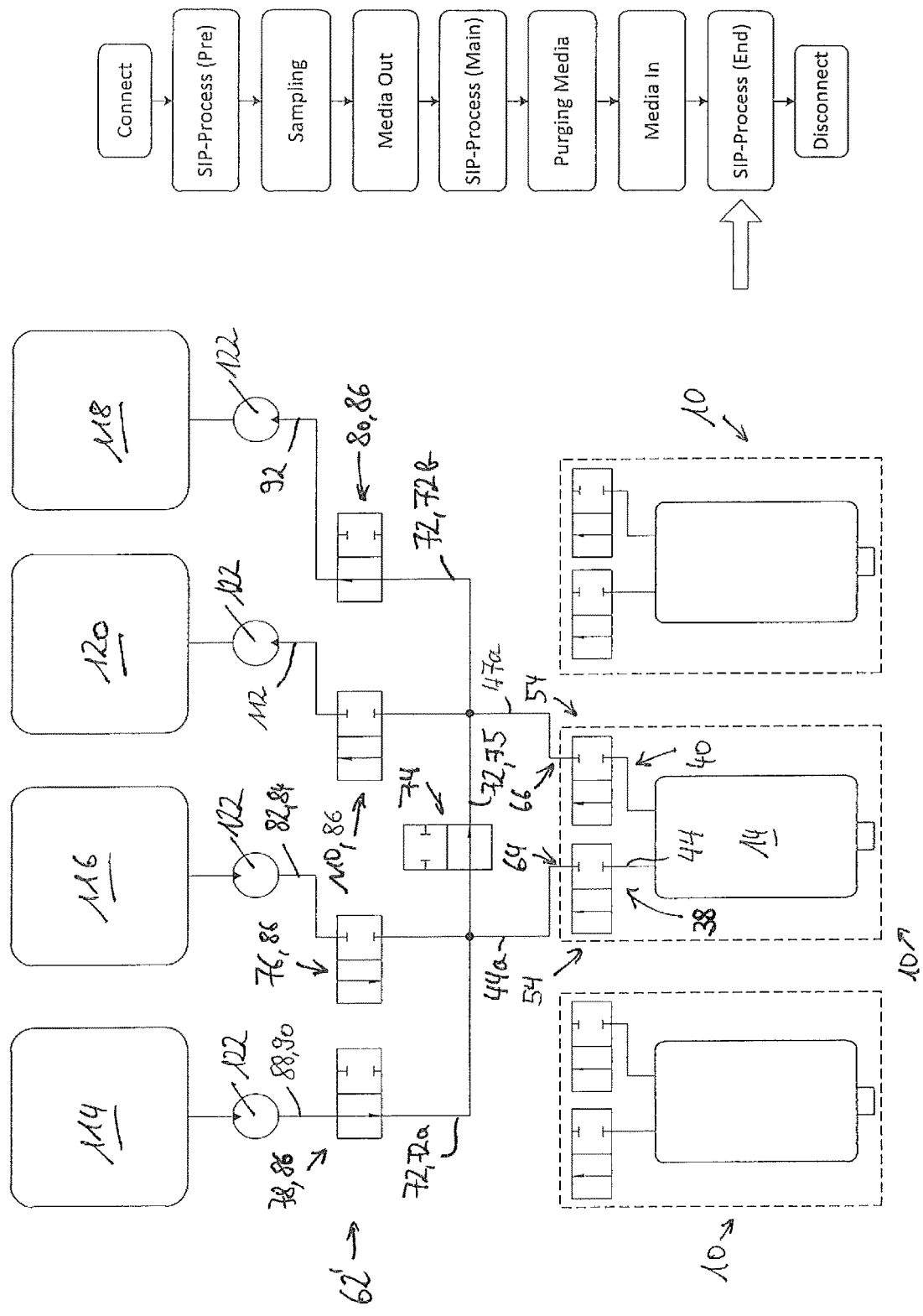

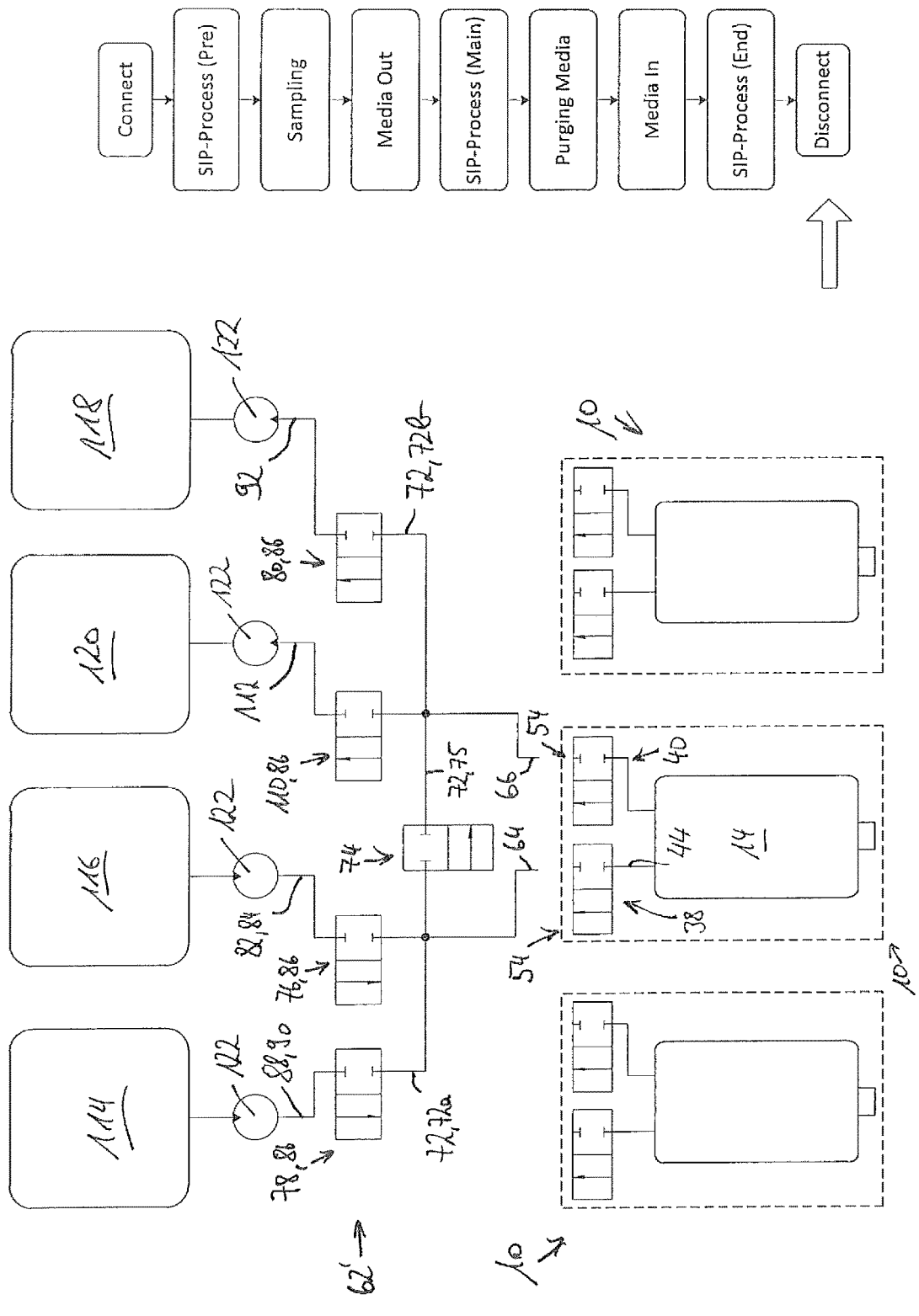

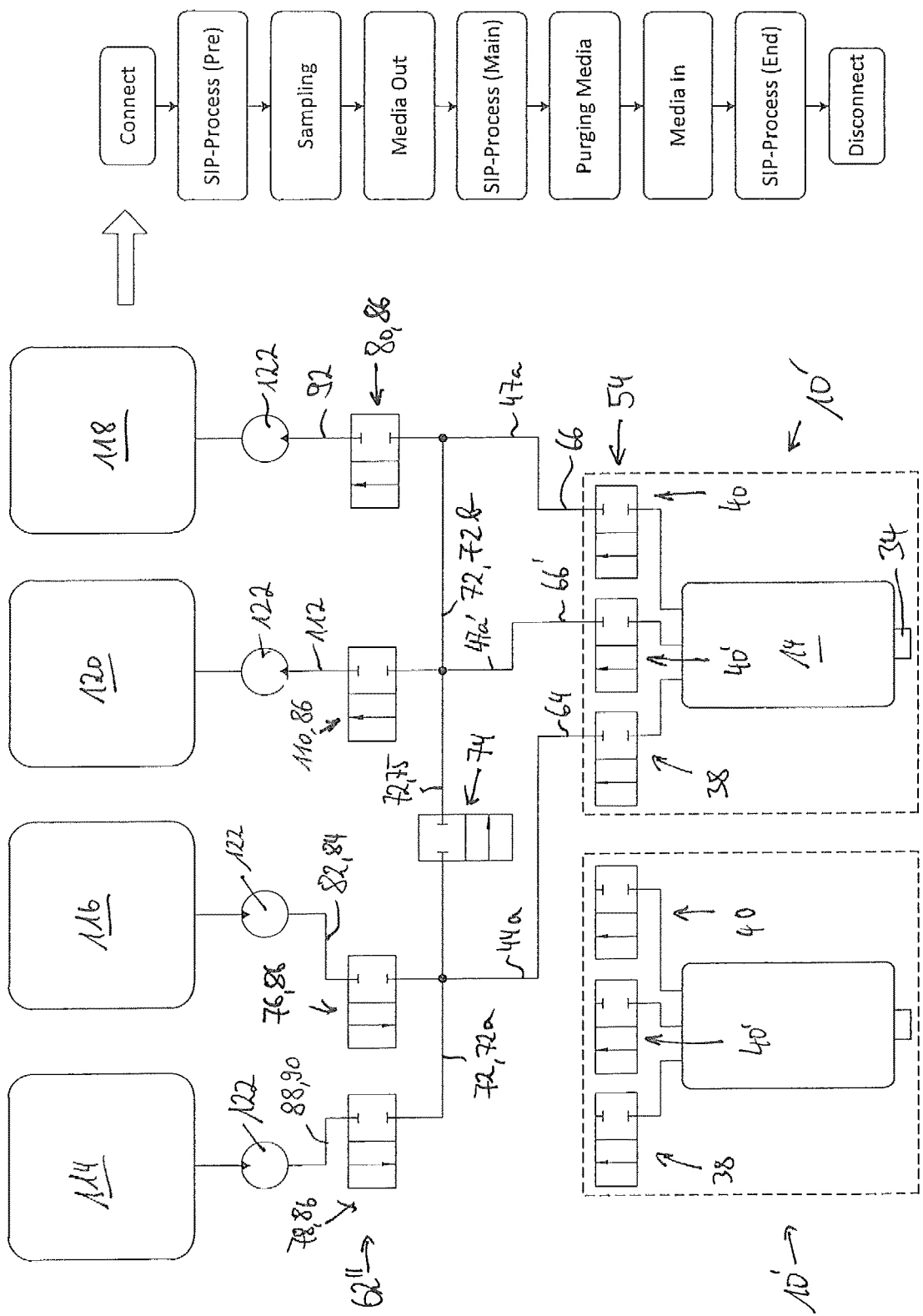

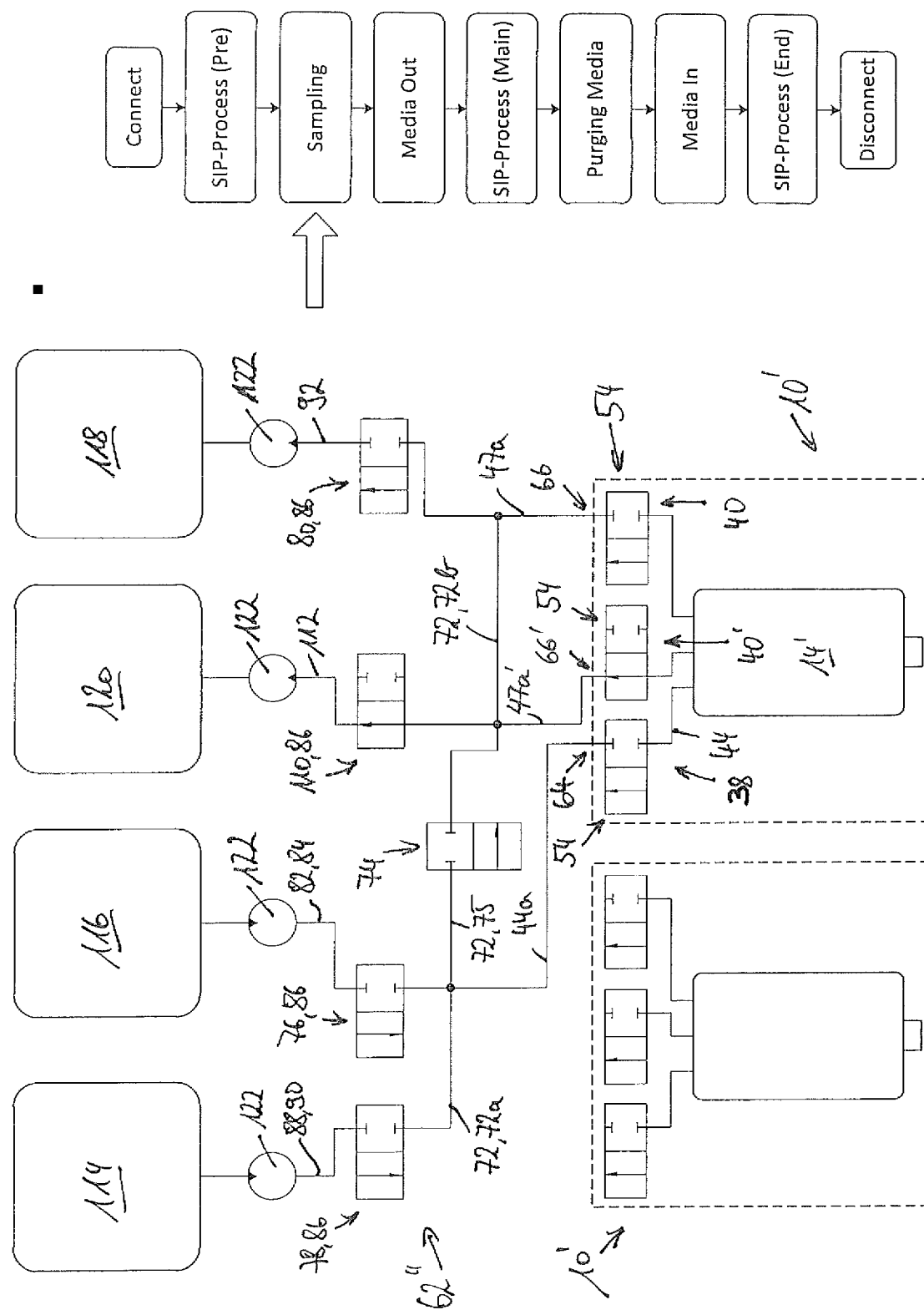

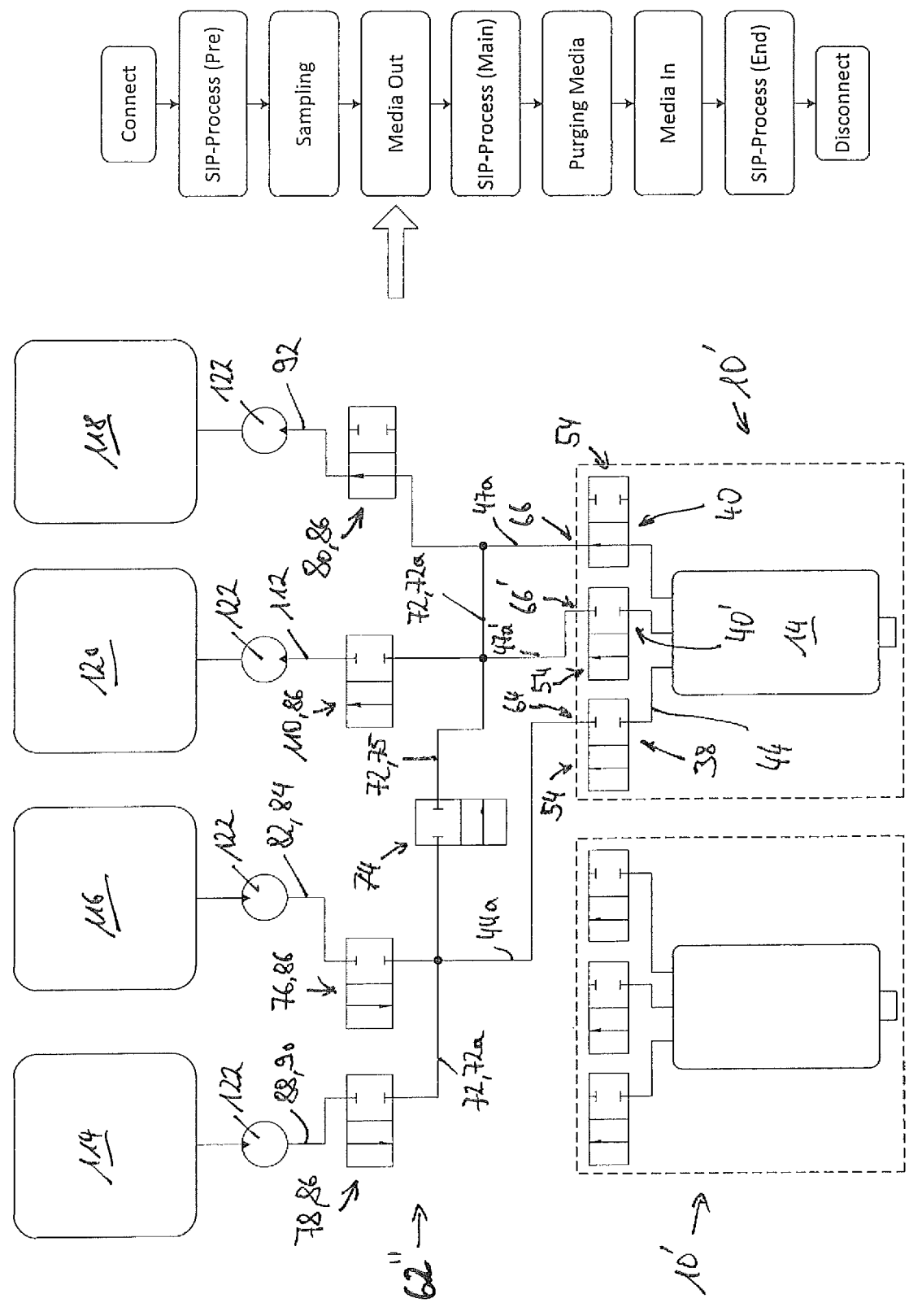

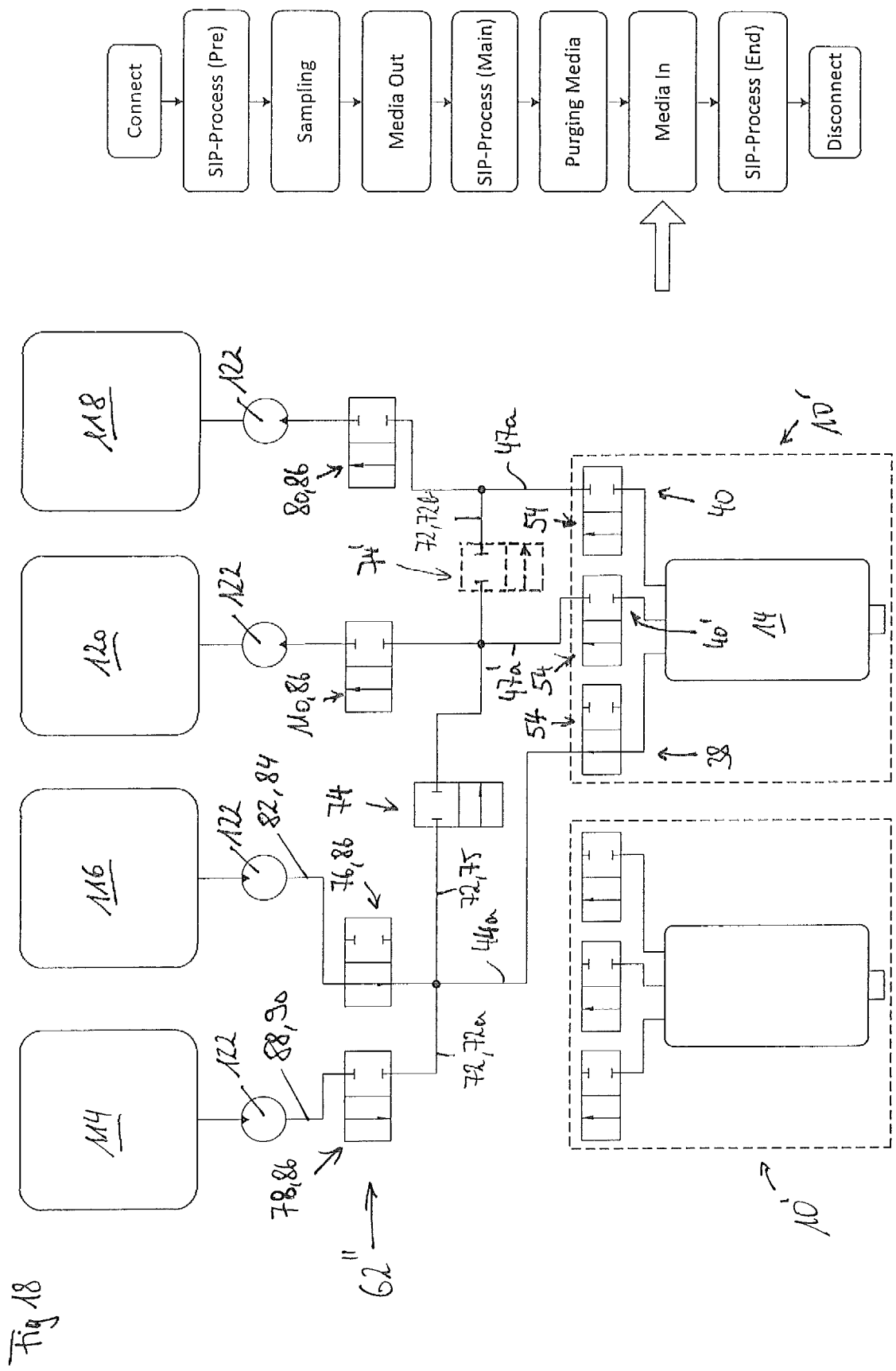

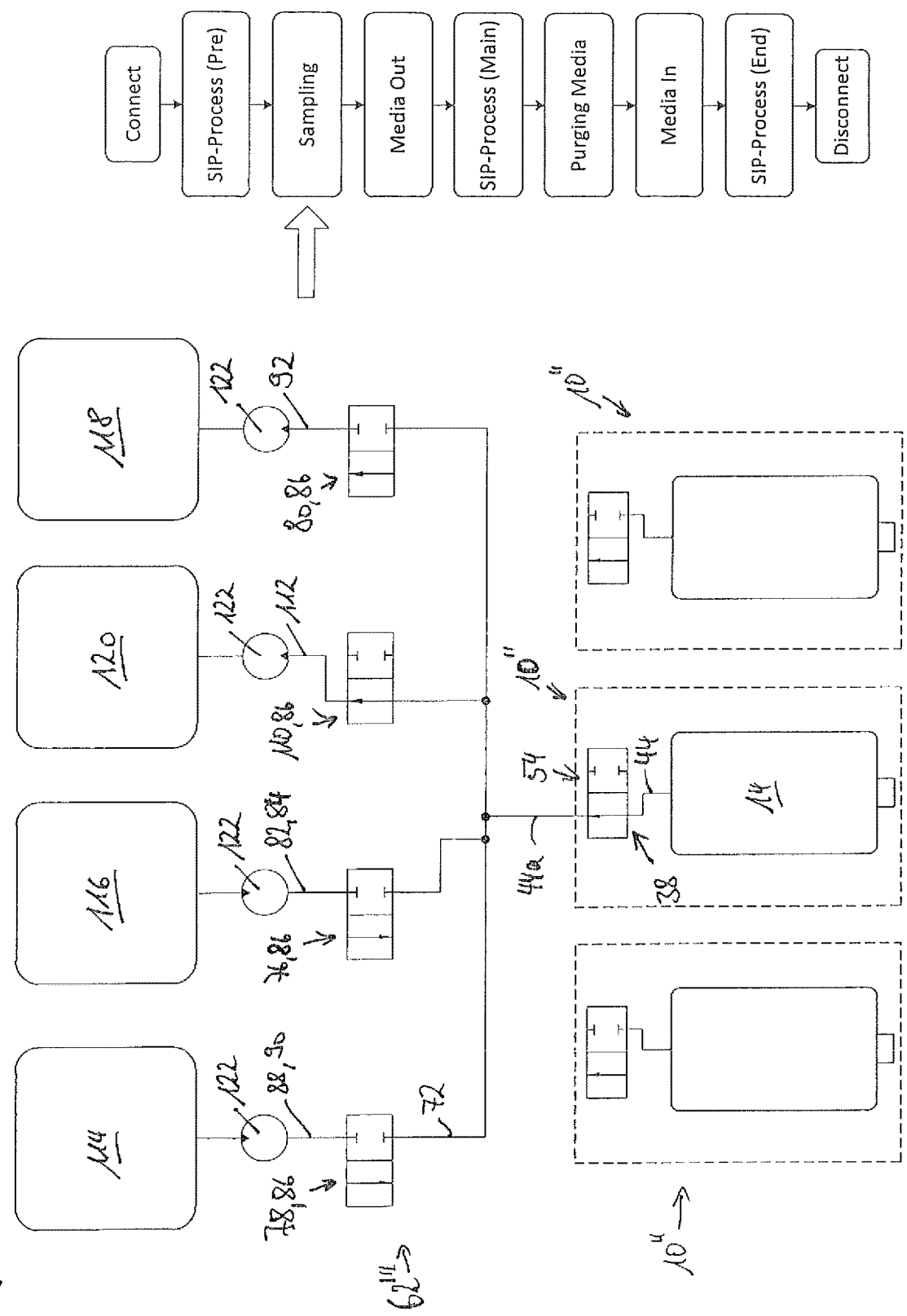

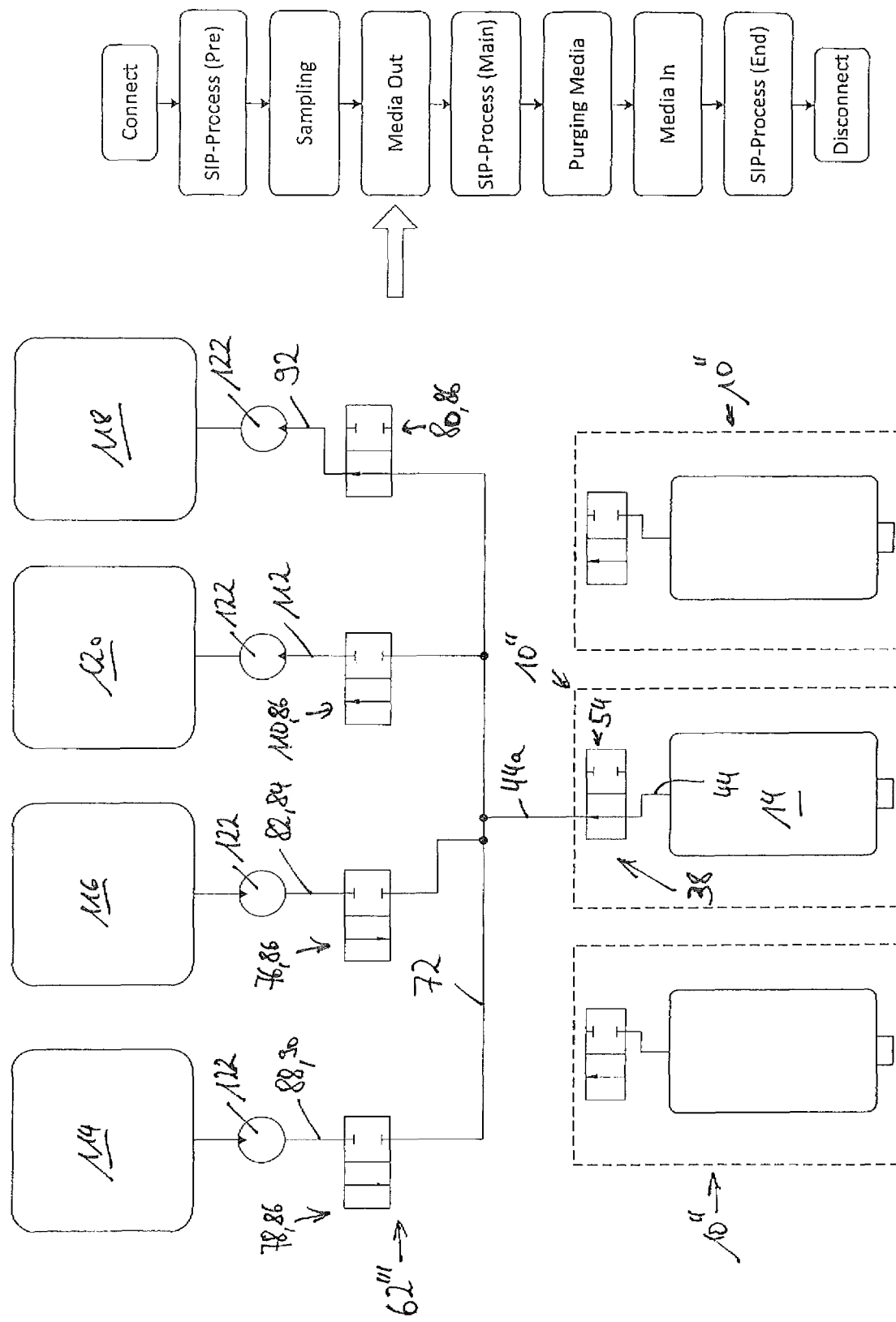

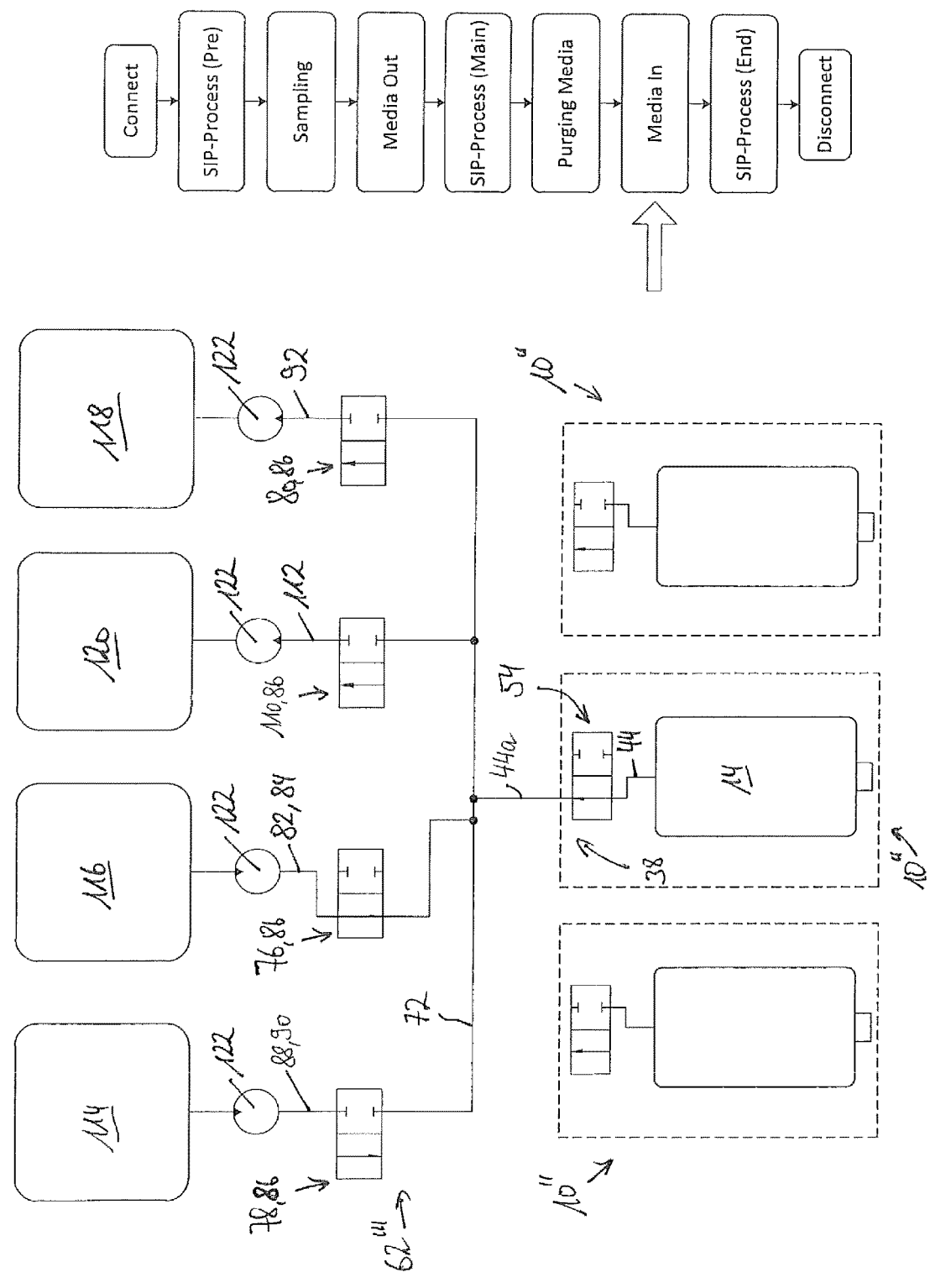

CELL CULTURING SYSTEM FOR CULTURING ADHERENT CELLS AND LIQUID SUPPLY INTERFACE COMPRISING A CELL CULTURE CONTAINER

CROSS-REFERENCE TO RELATED APPLICATION

This application is a divisional application of U.S. application Ser. No. 14/762,653 filed Jul. 22, 2015, which was the national stage application of International Application No. PCT/EP2014/051072 filed Jan. 21, 2014, both of which are expressly incorporated herein by reference.

BRIEF DESCRIPTION

The present invention relates to improvements in cell culturing systems comprising at least one cell culture container for collection and supply, i.e. particularly for cultivating with the goal of propagation, of adherent cells therein, comprising a nutrient medium reservoir for supplying the adherent cells in the cell culture container with nutrients, having a cleaning fluid reservoir for cleaning fluid flow paths or/and flow areas with the cleaning fluid, and comprising a liquid supply interface for coupling to the cell culture container.

The present application further relates particularly to the aforementioned liquid supply interface for a cell culture system for supplying cell cultures present in different cell culture containers having a nutrient medium. The present application further relates to cell culture containers, which are formed for provisional fluid-mechanical coupling with the liquid supply interface in order to introduce fresh nutrient medium into the cell culture container and to remove normally used or at least old nutrient medium from the cell culture container, once the liquid supply interface is coupled to a cell culture container in a fluid-mechanical manner.

Bioreactors specialized for their respective task and that are technically very complex have previously been used in the prior art for cultivating cells, which typically have a reactor area that can be heated by a heating mechanism integrated into the bioreactor and the content of which can be stirred or thoroughly mixed by a stirring mechanism permanently installed on the bioreactor.

A nutrient medium reservoir is typically provided on such types of bioreactors, which is permanently connected to the reactor area via lines as the core of cell cultivation. An additional line can go from the reactor to a discharge or a disposal collection container. This line is also typically permanently connected to the reactor area. Thus, there is a 1:1 relationship between the number of reactor areas and the number of nutrient medium reservoirs.

When cultivating adherent cells, often disposable cell culture containers are used in the prior art, which are typically produced from transparent plastic so as to observe the cultivated cells and are completely passive, i.e. are formed without function units influencing the container area thermally (heating/cooling) or mechanically (stirring). To the extent that such type of disposable cell culture container requires a predetermined temperature control, this must occur in an incubator formed for this purpose or a similar device. A mixing of the liquid collected in the container area of such type of disposable cell culture container cannot be achieved with the disposable cell culture container in the absence of an agitator mechanism or optimally by a shaking the container.

The disposable cell culture containers in the prior art typically have a neck connecting piece equipped with an outer thread as the single access opening, which can be closed with a screw cap in the conventional manner. The disposable cell culture container can be filled, emptied, and even ventilated as desired through the neck connecting piece The disadvantage with the aforementioned bioreactors in a cell culture system is their high level of specialization for predetermined application cases, which means that it may be necessary to maintain different bioreactors even when cultivating merely a few different cell cultures.

After a single use of a bioreactor, in order to prevent contamination from cultures processed subsequently, the necessary cleaning effort for subsequent usage is either very extensive or the bioreactor will have to be taken out of operation and disposed of after a single use despite its relatively high procurement costs. Both scenarios increase significantly the costs associated with cell cultivation in such type of bioreactor.

When using the aforementioned disposable cell culture containers, the procurement and operating costs associated with them are significantly lower compared with the previously discussed bioreactors. However, such type of disposable cell culture containers often have a usable volume of less than 1 L and thus are only set up for manual operation on a laboratory scale, which keeps the yields achievable with said disposable cell culture containers undesirably low. Because of the single available access opening, which can be closed off with a screw top, the known disposable cell culture containers are not suitable for automation and thus, for use for culturing cells on an industrial scale.

Therefore, the object of the present invention is to overcome the aforementioned disadvantages of the prior art in cultivating adherent cells and to indicate technical teaching, which enables the cultivation of adherent cells with comparatively low costs (the reference variable in this case should be the costs per unit of weight of cell material obtained) and relatively higher yields.

This object is attained by the present invention by means of three main aspects, which are connected via a common inventive idea and which interact with one another, and different aspects relate to one and the same cell culture system.

According to a first aspect of the present invention, the aforementioned object is attained by a liquid supply interface for a cell culture system for supplying cell cultures found in different cell culture containers with a nutrient medium, in which the liquid supply interface according to the invention comprises the following:

a housing defining a flow area;

a first connection formation for the liquid-transferring connection of a first fluid line to the housing;

a second connection formation formed separately from the first for the liquid-transferring connection of a second fluid line with the housing; a third connection formation formed separately from the first two for the liquid-transferring connection of the housing with a third fluid line;

a coupling formation formed separately from the connection formations, which is formed for the producible and detachable liquid-transferring coupling contact according to the operation, with a corresponding counter-coupling formation of a cell culture container;

a first liquid flow path, which extends between the flow area and the first connection formation for introducing a first liquid from the outside into the flow area;

a second liquid flow path, which extends between the flow area and the second connection formation for introducing a second liquid different from the first from the outside into the flow area; a third liquid flow path, which extends between the flow area and the third connection formation for removing a liquid from the flow area; and a coupling flow path, which extends between the flow area and the coupling formation in order to remove a liquid from the flow area and/or to introduce it to said flow area via the coupling formation, in which the first, the second, and the third liquid flow path each have a valve configuration, which is completely surrounded—with the exception of the respective liquid flow path—by the housing, incorporated in it, without a continuous signal- or/and power-transferring physical connection surrounded by the valve configuration up to the outside of the housing;

in which a control configuration with a signaling means generating an electric or/and magnetic or/and electromagnetic field is allocated to each valve configuration, the field of which acts upon a correspondingly field-sensitive counter signaling means of the valve configuration without contact, in which each valve configuration can be switched between a blocked position, in which the valve configuration interrupts a liquid flow in the liquid flow path in which it is arranged, and an outlet position in which the valve configuration enables a liquid flow, by means of the field acting upon its counter-signaling means.

The aforementioned connection formations makes it possible to introduce liquids into the housing of the liquid supply interface and thus into the flow area and to remove it from said area. These liquids may be, for example, a nutrient medium and a cleaning fluid. Furthermore, fluid may be removed from the housing via one of the connection formations, i.e. from the flow area defined in the housing.

The liquid supply interface can be coupled with a cell culture container in a liquid-transferring manner with the at least one coupling formation. Thus, it is possible to place one and the same liquid supply interface in coupling contact one after the other with one of a plurality of cell culture containers in a liquid-transferring manner and thereby obtain the possibility of introducing liquid from the flow area of the liquid supply interface into the respectively coupled cell culture container or to remove it from said container into the flow area of the liquid supply interface. For example, used nutrient medium or nutrient medium that is no longer fresh can be transferred from a coupled cell culture container in a liquid-transferring manner to the coupling formation and placed in the flow area via the coupling flow path and routed from said flow area through the aforementioned third liquid flow path from the flow area through the third connection formation out to a discharge or a collection container.

Due to the three connection formations formed separately from one another, as is explained in detail in the following, the requirement that the liquid supply interface be in contact with different cell culture containers is met without the risk of a cell culture container being cross-contaminated with contaminated contents from a cell culture container coupled downstream. Because, for example, nutrient medium from a nutrient medium reservoir can be introduced into the flow area via the first liquid flow path by means of the first connection formation and from the flow area then further routed into a cell culture container connected in a liquid-transferring manner via the coupling flow path. The corresponding valve configurations can be switched between the blocked position and the outlet position without mechanical access to a valve body or/and valve seat of the valve configuration being necessary through the control configuration in a contactless manner via the field-generating signaling means.

As previously mentioned, desired nutrient medium can likewise no longer be routed through the coupling formation along the coupling flow path within the cell culture container into the flow area and diverted from the flow area to a discharge or collection container via the third liquid flow path.

Due to the provision of the second connection formation with the second liquid flow path formed there, a cleaning fluid, for example, can be introduced from a cleaning fluid reservoir connected to the second connection formation in a liquid-transferring manner into the flow area and removed from said area via the third liquid flow path. Thus, the flow area can be rinsed clean by the cleaning fluid in that the cleaning fluid flows from the second connection formation to the third connection formation through the flow area.

Due to the suitable positioning of the first, second, and third connection formation, it is possible to ensure that the cleaning rinsing covers all liquid flow paths, primarily those that are necessary for introducing fresh nutrient media into the cell culture container.

The introduction of fresh nutrient medium into a cell culture container coupled to the coupling formation is critical for undesirable cross-contamination when supplying different cell culture containers via one and the same liquid supply interface, because contaminated material can only reach a previously clean cell culture container via the coupling flow path. The removal of nutrient medium from cell culture containers, on the other hand, is not critical as long as the nutrient medium removed from a cell culture container is only being disposed of or will only be retained separately.

As previously referenced, the valve configurations may be switched advantageously in a contactless manner between the blocked position and the outlet position by a field-generated signaling means, which interacts with a correspondingly field-sensitive counter-signaling means of the valve configuration. Thus, the valve configuration can be hermetically sealed from the environment. The valve configurations or components themselves therefore only come into contact with liquids that can flow along their respective liquid flow paths. Contamination of valve configurations from the exterior is prevented by the switching by means of field-generating signaling means and correspondingly field-sensitive counter-signaling means if there is no exterior connection, on the other hand.

If it is revealed in this application that a valve configuration is incorporated in the housing without a continuous signal- or/and energy-transferring physical connection from the valve configuration up to the exterior of the housing, then this case includes mechanical signal- or/and energy-transferring through rod linkage or/and gearbox, screw or spindle drives, and the like, with which a valve body of the valve configuration can be lifted up from its valve seat from outside of the housing and can be set back down on it. The phrase continuous signal- or/and energy-transferring physical connection also includes wires running from the exterior of the housing to the valve configuration or a valve drive, with which electrical power can be routed to an electric drive, with which, in turn, a valve body of the valve configuration can be driven in order to generate movement between the blocked position and the outlet position.

In order to prevent any influence from the outside on the valve configurations of the connection formations, each valve configuration with valve seat and valve body should therefore be completely surrounded by the housing, without said surrounding being interrupted by a physical signal- or/and energy-transferring connection. The single exception to the complete surrounding of the valve configuration by the housing are the liquid flow paths allocated to the valve configurations, which must remain free of housing material in order to enable the flow of liquid along the respective liquid flow path.

Due to a corresponding switching of the control configuration, the valve configurations of the liquid supply interface may be switched, for example, such that initially after establishment of a liquid-transferring coupling contact of the coupling formation with the corresponding counter-coupling formation of a cell culture container, the flow area is flushed with cleaning fluid via the second and the third liquid flow path. Thereby, any valve configurations at the corresponding counter-coupling formation of the cell culture container can also be cleaned.

Following this, nutrient medium can be removed from the cell culture container via the coupling flow path and the third liquid flow path. Subsequently, there can be another flushing of the flow area of the liquid supply interface with cleaning fluid via the second and the third liquid flow path thereby effecting renewed cleaning of the flow area.

Following this, there may be an additional cleaning rinse with fresh nutrient medium via the first and the third liquid flow path of the flow area of the liquid supply interface in order to remove any residue of cleaning fluid from the liquid supply interface.

After this, fresh nutrient medium may be introduced to the respectively coupled cell culture container via the first liquid flow path and the coupling flow path.

Subsequently, the cell culture container now freshly supplied with nutrient medium can be uncoupled from the liquid supply interface, possibly after an additional cleaning rinse with cleaning fluid via the second and the third liquid flow area, and connected to another cell culture container. The aforementioned rinsing and introduction and removal measures can then be repeated. This can be repeated for any number of cell culture containers, so that an n:1 number relationship can be realized between a plurality of cell culture containers and one nutrient medium reservoir.

Essentially, however, it is also possible to introduce only fresh nutrient medium into one cell culture container into only remove the nutrient medium existing there from the cell culture container. What is decisive is that the liquid supply interface between a liquid-transferring coupling contact with different cell culture containers can be flushed and cleaned with cleaning fluid in sufficient measure by the corresponding flush procedures in order to prevent the risk of cross-contamination that can occur during coupling one and the same liquid supply interface to different cell culture containers.

To facilitate the maximum effective cleaning of the flow area of the liquid supply interface, a provision according to an advantageous further embodiment of the present invention is that the flow area extend essentially in a straight line at least between the connection formation, which is formed for connecting the liquid supply interface with a cleaning fluid reservoir—which is preferably the second connection formation—and the connection formation, which is formed for connecting the liquid supply interface with a discharge or disposal container or the like—which is preferably the third connection formation. In order to prevent intermeshing areas, the flow area is preferably formed essentially circular-cylindrically. The circular-cylindrical formation may, however, deviate from an ideal circular-cylindrical shape in those areas in which the first, the second, or the third liquid flow path or the coupling flow path feeds into the flow area.

In order to expand the functional scope of the liquid supply interface discussed here to include the option of removing samples of media from a cell culture container, in addition to the previously mentioned functions, it may be provided according to a further embodiment of the present invention that the liquid supply interface further comprise the following:

a fourth connection formation formed separately from the remaining three for the liquid-transferring connection of the housing to a fourth fluid line and a fourth liquid flow path, which extends from the flow area between the flow area and the fourth connection formation for removing a liquid.

The fourth liquid flow path can, for example, lead to a sample collection container or a sample collection outlet, at which the media sample removed from the cell culture container is collected for further processing. Through such type of sample collection, it can be determined, for example, by means of chemical analysis of the nutrient medium removed from a cell culture container, whether the nutrient medium is sufficiently pure enough, the cultivated cell cultures have the life cycles as expected, and so on and so forth.

The fourth liquid flow path preferably also has a valve configuration the same as the first, the second, and the third liquid flow path. To avoid unnecessary repetitions, reference is hereby made to the previous and the following description of the valve configuration of the first, the second, and the third liquid flow path, which also applies to the valve configuration of the fourth liquid flow path, regarding the embodiment of the valve configuration of the fourth liquid flow path and the associated technical advantages.

One or more of the first to fourth connection formation may be formed as a detachable connection formation to which a fluid line is connectable to the housing of the liquid supply interface in a detachable manner, for example through detachable plug connections, as are known in the prior art. This may be helpful when different fluid lines are to be connected to one or more connection formations in a liquid-transferring manner at different times. This is, however, not the case with the preferred use of the liquid supply interface discussed here for a cell culture system for supplying different cell culture containers with nutrient medium. For reasons of increased operational safety and primarily for the improvement of hygiene, it is therefore preferable to form each of the first to fourth connection formations as a permanent connection formation, to which first to fourth fluid lines are permanently connected to the housing of the liquid supply interface in a liquid-transferring manner, according to the operation. For example, such type of connection formations can be implemented through screw connections, optionally with the intermediate configuration of sealing means, of connection formation and fluid line or through bonding, welding, soldering, or so on and so forth.

The phrase "permanently connected in a liquid-transferring manner according to the operation" in this case means that, except for a case of damage or maintenance, once a fluid line is connected with a connection formation, it is not again detached during the conventional operation service life of a liquid supply interface. This is contrary to the coupling formation, which is precisely formed according to the operation frequently coupled to a counter-coupling formation of a cell culture container in a liquid-transferring manner and will be again detached from it.

A further increase in the hygiene that can be achieved in the liquid supply interface of the present application can take place by providing multiple coupling formations and by separating the function thereof. Thus, the previously discussed coupling formation may, for example, be a first coupling formation through which, for example, exclusively fresh nutrient medium is introduced in a cell culture container coupled thereto during operation of the liquid supply interface. Furthermore, the liquid supply interface may have a second coupling formation formed separately from said first coupling formation, through which, for example, exclusively nutrient medium is removed from a coupled cell culture container when the coupling contact is established.

In general, in order to improve hygiene according to an advantageous further embodiment of the present invention, the aforementioned coupling formation may have a first coupling formation, the liquid supply interface may have a second coupling formation formed separately from the first, which is formed for coupling contact that is producible according to the operation and detachable in a liquid-transferring manner with a corresponding second counter-coupling formation of the cell culture container, and the liquid supply interface then may have a second coupling flow path, which extends between the flow area and the second coupling formation, in order to remove liquid from the flow area or/and to introduce it to said area via the second coupling formation.

The aforementioned advantageous functional separation of the two coupling formations of a further-embodied liquid supply interface as previously advantageously described can thereby be even further improved with respect to the achievable hygiene standard in that the liquid supply interface has a connection flow path extending between the first and the second coupling formation and the liquid supply interface in said path has a separating valve configuration, which is completely surrounded by the housing and incorporated in it, without a continuous signal- or/and power-transferring physical connection from the separating valve configuration up to the exterior of the housing—with the exception of the connection flow path, in which a control configuration with a signaling means generating an electric or/and magnetic or/and electromagnetic field is allocated to the separating valve configuration, the field of which acts upon a correspondingly field-sensitive counter-signaling means of the separating valve configuration without contact, in which the separating valve configuration can be switched between a blocked position, in which the separating valve configuration interrupts a liquid flow in the connecting flow path, and an outlet position, in which the separating valve configuration enables a liquid flow by means of the field, acting upon its counter-signaling means. The introduction of nutrient medium into a coupled cell culture container and the removal of nutrient medium from said container can be completely functionally and spatially decoupled from one another in a fluid-mechanical manner through the separating valve configuration. With the corresponding switching of the separating valve configuration, the flow area of the liquid supply interface can thus be subdivided into two sub-flow areas, in which exclusively cleaning fluid and fresh nutrient medium can flow through one sub-flow area and used nutrient medium and cleaning fluid and when the cleaning fluid is rinsed out, also fresh nutrient medium, can flow through the other sub-flow area, out of the cell culture container, upon corresponding activation of the separating valve configuration. Thus, a malfunction in the supply of the cell culture containers with fresh nutrient medium through contamination with previously discharged used nutrient medium from another previously coupled cell culture container can be avoided.

In order to clean the flow area, the separating valve configuration can be activated in its outlet position such that liquid can flow through for cleaning and also for subsequent rinsing of cleaning fluid through fresh nutrient medium of the entire flow area of cleaning fluid or/and fresh nutrient medium.

To prevent undesirable bypass malfunctions, it is advantageous if the connection flow path is the only liquid flow path extending between the first and a second coupling formation. This will also serve to prevent undesirable cross-contamination of cell culture containers coupled chronologically one after the other.

A suitable functional separation of the two coupling formations and the coupling flow paths allocated to them can be further supported in that the separating valve configuration is arranged such that the first and the second liquid flow path can be separated from the second coupling the flow path but not from a first coupling flow path by the configuration, and that the third liquid flow path can be separated from the first coupling flow path but not from the second coupling flow path by the configuration. In this case, each sub-flow area has a coupling flow path and at least one liquid flow path, and a coupling formation and at least one connection formation is connected to each sub-flow area in a liquid-transferring manner.

More precisely, preferably the first and the second liquid flow path feed into one sub-flow area and the third liquid flow path feeds into the respectively other sub-flow area.

Then, if the aforementioned configuration of the liquid flow paths and/or the connection formations allocated to them is maintained, i.e. introduction of fresh nutrient medium into the flow area via the first coupling flow path, introduction of a cleaning fluid into the flow area via the second liquid flow path, and discharge of liquids from the flow area via the third liquid flow path for example, the one sub-flow area can be used for introducing fresh nutrient medium into a coupled cell culture container and the respective other sub-flow area can be used to discharge used nutrient medium from the coupled cell culture container, in which these two functions are advantageously hygienically separated from one another due to the separating valve configuration.

Then, if the previously mentioned fourth connection formation is formed with a fourth liquid flow path at the liquid supply interface, the fourth liquid flow path advantageously feeds into the same sub-flow area as the third liquid flow path provided for discharging liquid from the flow area. This enables symmetrical distribution of liquid flow paths and coupling flow paths in the two sub-flow areas formed by the separating valve configuration.

Because the possibility of contaminating the discharging liquid flow path, for example through metabolism of products in these cell cultures within the cell culture container, is greater than with the liquid flow paths starting from a reservoir with fresh liquid (for example nutrient medium or/and cleaning fluid) when discharging fluid from a cell culture container coupled to the liquid supply interface, it can be advantageous, when a separate option for removing media samples from a coupled cell culture container is desired, to provide separate coupling flow paths for removing media samples from one cell culture container, on one hand, and for merely disposing of used nutrient medium, on the other hand.

Accordingly, there may be a design option according to a further embodiment of the present invention for implementing this hygiene-increasing measure such that the liquid supply interface has a third coupling formation formed separately from the first and the second and a third coupling flow path, which extends between the flow area and the third coupling formation, in order to discharge liquid from the flow area or/and to introduce liquid into said area via the third coupling formation, in which the third coupling formation is formed for coupling contact that is producible according to the operation and detachable in a liquid-transferring manner with a corresponding third counter-coupling formation of the cell culture container.

In turn, it may be advantageous from the previously mentioned considerations for improving the hygiene achievable with the liquid supply interface to design the individual coupling formations to be separable from one another in a fluid-mechanical manner by the separating valve configurations. To this end, it may be provided according to a further embodiment of the prevent invention that the aforementioned connection flow path be a first connection flow path and that the aforementioned separating valve configuration be a first separating valve configuration and that the liquid supply interface have a second connection flow path extending between the second and the third coupling formation and the liquid supply interface in said path have a separating valve configuration separate from the first, which is completely surrounded by the housing and incorporated in it, without a continuous signal- or/and power-transferring physical connection from the second separating valve configuration up to the exterior of the housing—with the exception of the connection flow path, in which a control configuration with a signaling means generating an electric or/and magnetic or/and electromagnetic field is allocated to the second separating valve configuration, the field of which acts upon a correspondingly field-sensitive counter-signaling means of the second separating valve configuration without contact, in which the second separating valve configuration can be switched between a blocked position, in which the second separating valve configuration interrupts a liquid flow in the second connecting flow path, and an outlet position, in which the second separating valve configuration enables a liquid flow, by means of the field, acting upon its counter-signaling means.

The separating valve configurations are preferably identically formed with the aforementioned valve configurations of the connection formations. This facilitates production and assembly of the liquid supply interface, because only one type of valve configuration must be produced and installed in the liquid supply interface and operated. In this respect, what was said regarding the aforementioned valve configurations and as follows applies to the separating valve configurations accordingly.

In turn, in order to prevent undesirable bypass malfunctions, it is preferably provided that the second connection flow path be the only liquid flow path extending between the second and the third coupling formation. This will ensure that the second and the third coupling formation can be separable from one another completely in a fluid-mechanical manner through a single separating valve configuration. Likewise, the previously mentioned measure means that the first and second coupling formation are completely separable from one another in a fluid-mechanical manner with the first separating valve configuration. To ensure reliable cleaning of the flow area, the connection formation connected to a cleaning fluid reservoir and the connection formation connected with a discharge or/and a disposal container are preferably provided such that, on the way from the first to the last, the first and the second separating valve configuration must be in the outlet position and thus in a position that the cleaning fluid flows through. This also ensures cleaning of the two separating valve configurations when the flow area is flushed.

In order to achieve the previous functions: Introduction of cleaning fluid, introduction of fresh nutrient medium, removal of liquid samples from a coupled cell culture container, and disposal of used nutrient medium with the least-possible risk of subsequent cross-contamination may be provided according to a further advantageous embodiment of the present invention in that the second separating valve configuration is arranged such that the third liquid flow path can be separated from the second coupling flow path but not from the third coupling flow path by said configuration, and that the fourth liquid flow path can be separated from the third coupling flow path but not from the second coupling flow path by said configuration, or that the fourth liquid flow path can be separated from the second coupling flow path but not from the third coupling flow path by said configuration, and that the third liquid flow path can be separated from the third coupling flow path but not from the second coupling flow path by said configuration.

The contactless signal- or/and power-transferring signaling means and counter-signaling means may use, for example, an electric field between each other for signaling or/and power transmission. To this end, the signaling means and the counter-signaling means may each comprise an electrode for establishing the electrical field between each other, in which the counter-signaling means may interact with a Piezo electrical actuator of the valve configuration such that the electric field established between the signaling means and the counter-signaling means brings about a structural change to the Piezo electrical actuator. With a suitable installation of the Piezo electrical actuator into the valve configuration, the structural change of the Piezo electrical actuator may, in turn, bring about an adjustment in the valve configuration between the blocked position and the outlet position. The material of the housing between the electrodes may act as a dielectric.

Due do the merely slight structural change of the Piezo electrical actuators, only slight flow gaps are expected to be established between the valve bodies and the allocated valve seat with this configuration. However, these may be sufficient in order to adjust the valve configuration between the blocked position and outlet position, i.e. to establish a state in which a liquid flow through the valve configuration is not possible (blocked position) and a state different from this in which such type of liquid flow is possible (outlet position).

Alternatively, the signaling means and the counter-signaling means may have a magnet and a ferromagnetic or/and magnetized component attracting its magnetic field. The effective magnetic field between the signaling means and the counter-signaling means may then cause shifting of the counter-signaling means. The shifting of the counter-signaling means may, in turn, cause an adjustment of the valve configuration between the blocked position and the outlet position. This may be implemented, for example, in the design in that the counter-signaling means is coupled to a valve body of a valve configuration for common movement, so that a shifting of the counter-signaling means lifts the valve body from its valve seat or places it back into contact at said seat. The counter-signaling means may also be in a particularly preferred embodiment of the valve body.

According to a further alternative, it may also be possible for the signaling means to comprise a magnet and for the counter-signaling means to comprise an electrically conducting component inductively attracting the magnetic field of the magnet of the signaling means. In this case, the magnetic field effective between the signaling means and the counter-signaling means can effect an induction in the counter-signaling means and this induction may, in turn, cause an adjustment in the valve configuration between the blocked position and the outlet position. For example, an actuator inductively placed in the housing, for example an electric motor or an electric magnet with shiftable anchor, may be supplied with sufficient electrical power through induction in order to drive the actuator to move. A valve body coupled to the actuator can thus be raised from its valve seat and placed back in contact with said seat.

Finally, in a technically more complex alternative, the signaling means may also comprise a transmitter of electromagnetic waves. These may be optical signals or radio signals. The counter-signaling means then comprises a corresponding receiver. The configuration may have a power storage unit surrounded by the housing and an actuator, which are coupled to one another with the counter-signaling means such that the counter-signaling means controls the actuator fed from the power storage unit for switching the valve configuration between the blocked position and the outlet position, depending on the electromagnetic waves received. In this case, signaling means and counter-signaling means are used like a remote control, somewhat comparable with the known remote control of a television or a remote-controlled toy. The power storage unit surrounded by the housing of the liquid supply interface, which according to definition should not be accessible from the exterior by a physical signal- or power-transmitting connection, can be inductively charged as an electrical power storage unit. The actuator may, in turn, be an electric motor or an electric magnet with moving anchor, in which, in the latter case, the anchor can assume different positions depending on the electrical state of the electric magnets. If the valve body of a valve configuration is coupled with a moving discharge part of the actuator for joint movement, the valve configuration can be switched between the blocked setting and the outlet setting in a prudent manner.

For reasons of simple and robust design with simultaneously particularly safe operation and ease of cleaning by the cleaning fluid that can flow through the signal area, that further embodiment of the aforementioned alternatives is preferred, according to which the signaling means and the counter-signaling means comprise a magnet, on one hand, and a ferromagnetic or/and magnetized component attracting its magnetic field, on the other hand, in which the counter-signaling means is preferably a valve body of the valve configuration for reasons of the least-possible number of components, which can be shifted away from its valve seat or/and toward said seat for sealing contact, under the effect of the magnetic field between the signaling means and the counter-signaling means.

In other words: the control configuration is formed for chronological or/and physical changing of a magnetic field starting from its at least one signaling means according to a preferred further embodiment of the present invention.

Furthermore, this preferred embodiment enables the valve configuration to be pretensioned magnetically in the blocked position and adjustable into the outlet position by the magnetic field starting from the signaling means. This pretensioning can be implemented in the design in that a valve seat of the valve configuration has a permanent magnet or ferromagnetic tension component, such that a magnetic tension force, particularly attracting force, is in effect between the tension component and the valve body, which tensions the valve body for sealing contact at the valve seat.

To ensure the most complete prevention of flow of the valve configuration and the blocked position, the valve seat may have an elastomer contact component, at which the valve body is directly positioned in the blocked position of the valve configuration. By using such an elastomer contact component, the valve body can penetrate into said contact component thus deforming the contact component due to the magnetic tensioning force and thus ensure flat contact of the valve body on the contact component. The elastomer contact component is preferably an annular component with a through-flow opening, which is closed by the valve body in the blocked position of the valve configuration and through which fluid can flow in the outlet position of the valve configuration. The magnetic tensioning force can be easily implemented in the design for deforming contact of the valve body at the elastomer contact component in that an attracting force is used as the magnetic tensioning force between the valve body and the tension component, in which it is sufficient to allocate the elastomer contact component between the valve body and the tension component. The elastomer contact component can be formed from rubber, close-cell foam, silicone, and the like. The tension component may consist of multiple sub-components, which however will make assembly more difficult. The tension component is preferably a permanent magnetic annular component, which surrounds an opening, through which liquid can flow in the outlet position of the valve configuration, as the preferred embodiment of the elastomer contact component.

For the aforementioned preferred case, in which the signaling means and the counter-signaling means comprise a magnet, on one hand, and a ferromagnetic or/and magnetized component attracting its magnetic field, on the other hand, the signaling means may comprise a locally shifted permanent magnet. By approximating the locally shiftable permanent magnet at the counter-signaling means, which is preferably the valve body itself, it can be removed from its pretensioning position, which is preferably the blocked position of the valve configuration, which is synonymous with the activation of the valve configuration in the outlet position. The only requirement for this is that the magnetic field starting from the permanent magnet of the signaling means acting on the valve body (counter-signaling means) be stronger than the magnetic field starting from the tension component, so that starting from a certain approximation of the permanent magnet of the signaling means, the magnetic force starting from it and acting on counter-signaling means, which is preferably the attracting force, is greater than the magnetic tensioning force starting from the tension component, so that the magnetic force starting from the permanent magnet prevails and causes an adjustment of the counter-signaling means, particularly of the valve body.

In addition to or alternatively to a locally shiftable permanent magnet, the signaling means may comprise an electric magnet, which generates a strong magnetic field that is chronologically different depending on its magnetic current. With such type of electric magnet, a magnetic field can also be generated through sufficiently strong magnetic current supply, the magnetic force of which overpowers the magnetic tensioning force of the tension component and thus ensures an adjustment of the counter-signaling means, particularly of the valve body. This will, in turn, cause switching of the valve configuration between the blocked position and the outlet position A particularly simple but effective control of the valve configuration of the liquid supply interface can then occur in that the control configuration has a plurality of sets of signaling means, in which the signaling means of a set each define a valve setting configuration of valve configurations of the liquid supply interface. Thus, a valve setting configuration can be precisely defined using a set of signaling means. Depending on which set of signaling means the counter-signaling means will approximate in the liquid supply interface, different valve setting configurations can thus be quickly and clearly activated with the same low incidence of errors. The aforementioned operation for removing liquid from a coupled cell culture container for cleaning and for flushing the liquid supply interface and for introducing fresh nutrient medium into a coupled cell culture container shows that, even in the most complex structure of the liquid supply interface with three coupling formations and four connection formations, essentially fixed valve setting configurations suffice, namely one for a basic position (for example all valve configurations in the blocked position) during a shifting of the liquid supply interface between two coupling contacts with different cell culture containers for the removal of medium from a cell culture container, for the cleaning of the liquid supply interface and/or its flow area, for the flushing of the same with fresh nutrient medium, for the removal of a medium sample from the cell culture container, and for the introducing of fresh nutrient medium into a coupled cell culture container. By providing six sets of signaling means or one set of signaling means with six different switching states if there are electric magnets as the signaling means, the liquid supply interface can thus be fully operated.

A compact placement of these sets of signaling means can be attained in the design in that the control configuration has a roller rotating around a roller axis, in which the plurality of signaling means sets are arranged distributed around the roller axis such that different valve setting configurations of the liquid supply interface can be adjusted by rotating the roller.

The approximation of the signaling means sets, for example, by rotating the aforementioned roller, may suffice for clearly engaging the individual valve configurations at a liquid supply interface. However, under some circumstances, there may be undesirable chronological offset between the switching of different valve configurations of the liquid supply interface.

The most precise possible switching of the valve configurations of the liquid supply interface can be achieved, in an advantageous manner, in that the control configuration has a placement configuration, which is arranged between a signaling means and valve configuration adjustable by the signaling means, in which the placement configuration has at least one magnet that is shiftable between an active position closer to the valve configuration and an inactive position closer to the signaling means, particularly permanent magnets.

For example, the placement configuration may have a shiftable magnet for each signaling means of a set of signaling means.

The at least one shiftable magnet is preferably pretensioned in one of its positions. To this end, it may have its own tensioning means. Said tensioning means may be omitted, however, according to a preferred embodiment if the pretensioning of the at least one shiftable magnet takes place by utilizing the force of gravity. Preferably, the at least one shiftable magnet is pretensioned in its inactive position so that it prevents an activation of the valve configuration allocated to it by the control configuration without any further measures. According to a previous preferred further embodiment of the present invention, the valve configurations are pretensioned in their blocked position so that flow-through of a valve configuration of the liquid supply interface is not possible without additional measures. Thus, a failsafe measure is implemented due to the further embodiment demonstrated here at the liquid supply interface.

Essentially it may also be possible to form the valve configurations such that they can be exclusively activated between the blocked setting and the outlet setting via the control configuration. However, it may be advantageous in certain operating positions if they are permeable in an outlet flow direction, regardless of their control configuration, due to sufficiently high liquid pressure in the allocated liquid flow path. Thus, filling of a cell culture container with fresh nutrient medium can be supported, for example, regardless of the switching of a valve configuration. The introduction of cleaning fluid into the flow area can likewise be supported.

According to an advantageous further embodiment of the present invention, it is thus intended for at least one part of the valve configurations, or preferably all valve configurations, to be adjustable, from the blocked position into the outlet position, in an outlet flow direction along the liquid flow path, in which they are arranged, by means of a predetermined liquid pressure difference; this does not apply to the opposite flow direction, in which preferably the outlet flow direction of the first and of the second liquid flow path is directed into the flow area and the outlet flow direction of the third liquid flow path is directed out of the flow area.

Advantageously, the cell culture containers at the counter-coupling formations are likewise equipped with valve configurations, as has been described previously. The arrangement of a valve configuration at the coupling flow paths can thereby be dispensed with when the coupling contact is detached. This means the coupling formation of the liquid supply interface preferably has no such type of valve configuration in order to preferably reduce the components necessary for forming the liquid supply interface.

By providing valve configurations in the counter-coupling formations of the cell culture container, this also ensures that the filling of the cell culture container does not change after the coupling contact between the liquid supply interface in the cell culture container has detached, but instead the coupling flow paths remain blocked on the cell culture container side by a valve configurations provided for there. Preferably, the control configuration for common joint movement is connected to the liquid supply interface. Thereby only the valve configuration and the counter-coupling formation of the respectively just-coupled cell culture container can advantageously even be switched off due to sufficient approximation of the control and valve configuration.

The object mentioned at the beginning is attained according to another aspect of the present invention by a cell culture system with at least one cell culture container for collecting and supplying adherent cells with a nutrient medium reservoir, with a cleaning fluid reservoir, and with a liquid supply point, as previously described and has been advantageously further demonstrated. The integration of the previously described liquid supply interface into the cell culture system with the remaining listed components takes place provided that:

the first connection formation connects the housing with the nutrient medium reservoir in a liquid-transferring manner and thus the first liquid flow path extends between the flow area and the nutrient medium reservoir;

the second connection formation connects the housing with the cleaning fluid reservoir in a liquid-transferring manner and thus the second liquid flow path extends between the flow area and the cleaning fluid reservoir;

the third connection formation connects the housing with a discharge in a liquid-transferring manner and thus the third liquid flow path extends between the flow area and the discharge;

the coupling formation for coupling contact, which is producible and detachable in a liquid-transferring manner according to the operation, is formed with a counter-coupling formation of the cell culture container;

the first liquid is the nutrient medium;

the second liquid is the cleaning fluid;

the coupling flow path is formed in order to remove nutrient medium from the flow area and supply it to the cell culture container or/and to remove it from said container and introduce it to the flow area via the coupling formation, in a state coupled with the counter-coupling formation.

This corresponds to the preferred connection pattern previously described in connection with operation of the liquid supply interface. Provided the previously mentioned advantages are indicated for the liquid supply interface, said advantages obviously also apply to the cell culture system, in which a liquid supply interface is accordingly connected at the nutrient medium reservoir, at the cleaning fluid reservoir, and at the closure. In the following description of the cell culture system, advantageous embodiments of the liquid supply interface and of the cell culture container that appear may obviously also be implemented at the liquid supply interface and/or at the cell culture container alone.

The cell culture container may further have the required number of delivery pumps order to convey the individual liquids into the fluid lines separately from one another.

The liquid-transferring coupling contact between the coupling formation of the liquid supply interface and the counter-coupling formation of the cell culture container may occur in a manner known from the prior art, for example through fluid-mechanical plug-socket connections, in which a pin-type, i.e. male plug or connecting piece is inserted into a female socket, so that when the fluid-transferring coupling contact is established, a longitudinal section of a formation comprising the coupling formation and the counter-coupling formation radially surrounds a longitudinal section of the respective other formation on the exterior. The coupling contact can be supported by a magnetic retaining means at the coupling formation and the counter-coupling formation. In addition or as an alternative to the magnetic retaining means, mechanical retaining means may also be provided, for example in the form of a destructible latch, which may be present between the coupling formation and the counter-coupling formation once the liquid-transferring coupling contact is established. The formations comprising the coupling formation and the counter-coupling formation may, however, exist without retaining means provided at the formations themselves, for example if a movement device, which moves the liquid supply interface between the cell culture containers to be coupled, exerts a force onto said formations when coupling contact is established between the coupling formation and the counter-coupling formation, which counteracts detachment of the coupling contact.

The applicant moreover reserves the right to look for separate protection for using a liquid supply interface, as has been previously described in its basic configuration and its preferred further embodiments, in a cell culture system for cultivating adherent cells.

As has been previously explained, the discharge at the longitudinal end, positioned away from the liquid supply interface, of the third liquid flow path may be a disposal drainage area or a disposal collection container, in which liquid is initially collected until a sufficient quantity is available in the disposal collection container and it is then routed to a disposal location.

Essentially, the cleaning fluid may be liquid or gas. In order to achieve the maximum cleaning effect, the cleaning fluid is preferably a cleaning liquid. The nutrient medium may essentially also be in liquid or gas form. Normally, the nutrient medium is present, however, as a nutrient liquid in order to achieve maximum nutrient density.

As previously shown, the cell culture system may have a sample collection device for grasping samples of the content of a cell culture container, in which samples removed from the cell culture container are collected until further processing thereof, for example through physical or/and chemical analysis and testing. In order to avoid undesirable contamination of the samples removed, the liquid supply interface may have the previously described forth connection formation. In this case, it is possible that the fourth connection formation to connect a housing with a sample collection device in a liquid-transferring manner on the cell culture system, and thus the fourth liquid flow path extends between the flow area and the sample collection device.

Because, in the cell culture system discussed in this case, cleaning of the flow area takes place by introducing the cleaning fluid into the flow area via the second connection formation and by removing the cleaning fluid from the flow area via the third connection formation, the most spatially extensive cleaning possible of the flow area can occur by flushing it with cleaning fluid in that a flow path in the flow area is the longest flow path between two valve configurations or between one valve configuration and one coupling formation, from the valve configuration of the second connection formation to the valve configuration of the third connection formation. In this case, the cleaning fluid covers the longest flow path in the flow area between introduction into the flow area and removal from said area, so that the cleaning fluid flows on said flow path flows through the largest possible part of the flow area and wets and flushes wall sections of same.

In doing so, during the described flushing of the flow area with cleaning fluid, at least the line routes, of the flow area, leading to additional connection formations can also be cleaned if, in the flow area, a flow path passes by the valve configuration of the first connection formation and optionally by the valve configuration of the fourth connection formation, from the valve configuration of the second connection formation to the valve configuration of the third connection formation.

The cleaning of the flow area of the liquid supply interface is thus based on strategies that are characterized in the prior art as "Sterilize-In-Place" (SIP) or also "Clean-In-Place (CIP). To facilitate the most effective SIP or CIP cleaning, which also cleans the valve bodies involved in the valve configurations in a flushing manner, it is advantageous if the valves bodies of the valve configuration of the first connection formation and optionally the valve bodies of the valve configuration of the fourth connection formation at least partially, or preferably at least more than halfway, penetrate into the flow path of the valve configuration of the second connection formation with respect to the valve configuration of the third connection formation. This further embodiment should expressly be understood as a further embodiment of the liquid supply interface on its own.

For the previously described reasons, it is advantageous if the cell culture container or containers have more than just one counter-coupling formation in order to achieve an increased hygiene standard, for example, through separating the nutrient medium feed and the nutrient medium discharge lines. According to an advantageous further embodiment of the cell culture system, it may be provided in concrete terms that the aforementioned counter-coupling formation of the cell culture container be a first counter-coupling formation, that the cell culture container have a second counter-coupling formation formed separately from the first counter-coupling formation, and that the cell culture system further have a liquid supply interface according to the previous pertinent description, provided that the first coupling formation is formed for coupling contact, which is producible and detachable in a liquid-transferring manner according to the operation, with the first counter-coupling formation, and that the second coupling formation is formed for a coupling contact, which is producible and detachable in a liquid-transferring manner according to the operation, with the second counter-coupling formation of the cell culture container, as well as that the second coupling flow path extends between the flow area and the second coupling formation in order to remove nutrient medium from the flow area and supply it to the cell culture container or/and to remove it from said container and introduce it to the flow area via the second coupling formation, when there is coupling contact established with the second counter-coupling formation. The previous generally applies accordingly with respect to the counter-coupling formation and/or the coupling formation to those formed from the first and the second counter-coupling formation and from the first and the second coupling formation.

Because, when a medium existing in the cell culture container is intended for proper hygienic sample removal, said medium may be implemented at a further advantageously embodied cell culture system in that the cell culture container has a third counter-coupling formation formed separately from the first and second, and that the cell culture system has a liquid supply interface according to the previous pertinent description, provided that the third coupling formation is formed for coupling contact, which is producible and detachable in a liquid-transferring manner according to the operation, with the third counter-coupling formation of the cell culture container, as well as that the third coupling flow path extends between the flow area and the third coupling formation in order to remove nutrient medium from the flow area and supply it to the cell culture container or/and to remove it from said container and introduce it to the flow area via the third coupling formation, when there is coupling contact established with the third counter-coupling formation.

In order to prevent media from escaping from the cell culture container after the liquid-transferring coupling contact has been detached between the at least one coupling formation of the liquid supply interface and the at least one counter-coupling formation of the cell culture container, it is possible, with a further embodied cell culture system, for at least one counter-coupling formation, or preferably every counter-coupling formation, of the cell culture container to have a container valve configuration.

Accordingly, the coupling formation may be free of a valve configuration at the liquid supply interface. The container valve configuration is preferably set up as the extensively discussed valve configurations of the connection formations, to which description express reference is hereby made regarding discussion of the container valve configurations.

Consequently, it is preferable when the counter-coupling formation forms a male plug and the free coupling formation of the liquid supply interface forms a female socket for reducing the number of components, necessary for reducing their formation, preferably of a valve configuration.

Preferably, in order to achieve a high hygiene standard, the container valve configuration is completely surrounded by the counter-coupling formation and the housing, with the exception of the liquid flow path interfusing the coupling formation and the counter-coupling formation, without a continuous signal- or/and power-transferring physical connection from the container valve configuration up to the exterior of the counter-coupling formation and of the housing of the liquid supply interface, when coupling contact is established between the counter-coupling formation and the coupling formation.

If the coupling contact is not established, the container valve configuration may lie exposed at least partially at the counter-coupling formation. It may be covered by a cover, which can be removed from the counter-coupling formation and be placed on said counter-coupling formation, between the times when there is coupling contact with a coupling formation. To this end, a suitable placement and removal device may be provided, which is either independently arranged in the cell culture system or formed to move jointly with the liquid supply interface. This removal and placement device may be formed, for example, by a multi-axis robot or by a moving gripper in a removal and placement device with the attachment at the liquid supply interface for common movement with said interface. This gripper may be driven, for example, by a spindle drive or a dual-acting piston-cylinder arrangement for moving in the removal and placement direction.

According to the preferred similar embodiment of the valve configurations of the connection formations and the at least one container valve configuration, the latter may also be switchable between a blocked position and an outlet position by the control configuration of the liquid supply interface. Thus, it is sufficient to provide only one common control configuration for the valve configurations of the cell culture container and for those of the liquid supply interface. A requirement for this is that the container valve configuration be pretensioned in the blocked position and then only have to be switched when a liquid-transferring coupling contact has been established between the counter-coupling formation supporting the container valve configuration and a coupling formation of the liquid supply interface. Then the at least one container valve configuration and the valve configurations of the liquid supply interface may be spatially so tightly sealed with one another such that the switching can be easily implemented through a single common control configuration.

The possibility of being able to clean the at least one container valve configuration as well with cleaning fluid from the second to the third connection formation when flushing the flow area can thereby be attained in that a flow path, in the flow area, passes from the valve configuration of the second connection formation to the valve configuration of the third connection formation at the at least one container valve configuration, or preferably at all container valve configurations, when coupling contact is established between the at least one coupling formation of the liquid supply interface and the at least one counter-coupling formation of a cell culture container. In addition, this will enable the cleaning of at least one part of the coupling flow paths feeding into the flow path from the second to the third connection formation.

A cleaning of particularly the container valve configurations by flushing the flow area can thereby be achieved in the design or even improved in that, when coupling contact is established between the at least one coupling formation of the liquid supply interface and the at least one counter-coupling formation of a cell culture container, the valve body of the at least one container valve configuration, or preferably said valve body of all container valve configurations, protrudes at least partially, or preferably at least more than halfway, into the flow path from the valve configuration of the second connection formation to the valve configuration of the third connection formation. The container valve configurations with their valve bodies thus preferably protrude precisely as far into the flow path from the valve configuration of the second connection formation to the valve configuration of the third connection formation as the valve bodies of the valve configurations of the connection formations. The advantages mentioned in connection with the previous valve configurations, particularly with the cleaning thereof, also apply to the container valve configurations.

To facilitate assembly, operation, and maintenance, the cell culture system can be further embodied such that all valve configurations provided in the liquid supply interface, or preferably also all valve configurations provided in the at least one cell culture container, are essentially constructed identically.

Advantageously for a cleaning of the flow area, the flow path extends from the valve configuration of the second connection formation to the valve configuration of the third connection formation in a straight line, or particularly preferably along an essentially circular-cylindrical channel in order to prevent intermeshing points. The relative movement direction of the valve bodies of the valve configurations of the second and of the third connection formation when they switch between the blocked position and the outlet position preferably extends along the flow path from the valve configuration of the second connection formation to that of the third connection formation. The valve bodies of these valve configurations can thereby be covered by cleaning fluid on the largest possible area when the flow area is flushed and thus be cleaned particularly well and reliably.

The previously mentioned elastomer contact component at which the valve body of a valve configuration makes contact in its blocked position may not only be used for sealing the passageway through the valve configuration but moreover can also be used for sealing off a connection formation radially to the exterior. To this end, there may be a design provision in at least one connection formation, or preferably in a plurality of connection formations, that an annular axial end face of the elastomer contact component, as a sealing surface that surrounds the liquid flow path allocated to the connection formation radially to the exterior, make contact, deformed, at a counter-sealing surface. The counter-sealing surface in this case may either be formed at the housing of the liquid supply interface or may be part of the fluid line connected in a liquid-transferring manner to the housing of the liquid supply interface at the respective connection formation.

In a similar manner, the container valve configuration may also be provided at a counter-coupling formation of a cell culture container and be used to seal off the coupling contact established between the counter-coupling formation and the allocated coupling-formation radially to the exterior with an annular axial end face. To this end, there may be a provision that an annular axial end face of the elastomer contact component of the container valve configuration make contact, deformed, at a counter-sealing surface of the liquid supply interface as the sealing surface surrounding the liquid flow path allocated to the coupling formation radially to the exterior, when coupling contact is established between the at least one coupling formation of the liquid supply interface and the at least one counter-coupling formation of a cell culture container.

Preferably, the elastomer contact component may have a channel passageway surrounded by an elastomer material, in which preferably the elastomer contact component has a conical recess, in which the valve body is accommodated and at the negative-conical wall of which the valve body has sealing contact in the blocked position of the valve configuration. The valve body in this case may be a cone itself or preferably a sphere, due to the symmetry and the associated orientation invariance.

If there is a conical recess provided at the elastomer contact component, which widens down to an exposed longitudinal end pointing away from the tension component, the annular axial end face remaining at the longitudinal end of the conical recess may be particularly easily used for sealing at the counter-sealing surface, as previously shown.

An essential advantage of the cell culture system according to the invention is that it may have more cell culture containers than liquid supply interfaces and media and liquid reservoirs such that a plurality of separately formed cell culture containers can be supplied from one and the same nutrient medium reservoir. In doing so, five liquid supply interfaces, for example, may be sufficient for the entire cell culture system. The risk of collision when moving the liquid supply interfaces between the individual cell culture containers can be further reduced by reducing the number thereof. Thus, it is preferable when the cell culture system has no more than three liquid supply interfaces. In actuality, even one liquid supply interface may be sufficient in order to supply a number of cell culture containers with fresh nutrient medium and to remove used nutrient medium from the cell culture containers.

In order to move the at least one liquid supply interface between the cell culture containers to be coupled to it, the cell culture system may have a movement device. Said device is formed in order to bring the at least one liquid supply interface into liquid-transferring coupling contact with different cell culture containers one after the other. A potential design of such a movement device may be a cross table configuration with movement slides provided thereon, which provide a movement plane that is orthogonal with respect to the cross table plane, so that a liquid supply interface arranged on such type of movement device can be moved in at least three spatial directions that are linearly independent. Alternatively, and this is preferred, the movement device may be a multi-axis robot, which offers a multitude of translational and rotational movement options depending on its number of axes. Other movement devices that enable the approaching of different locations in space are known to the average person skilled in the art from the prior art.

The object mentioned at the beginning is, moreover, attained as well by a cell culture container for an embodied cell culture system as previously described. Said cell culture container is formed for interacting with the previously described liquid supply interface for establishing and detaching a coupling contact with a coupling formation of the previously mentioned type.

Said cell culture container has a container body comprising a culture volume with a fill opening through which gas, liquid, paste, or/and solid bodies can be filled into the container body and removed from said container body. Thus, the aforementioned fill opening can be used in addition or as an alternative or even as a ventilation opening.

According to the invention, such type of cell culture container is formed for establishing and detaching a coupling contact with a liquid supply interface such that the cell culture container additionally has at least one counter-coupling formation formed separately from the fill or/and ventilation opening, which is formed for establishing and detaching a coupling contact with a corresponding coupling formation of the liquid supply interface, in which a delivery liquid flow path extends between the at least one counter-coupling formation and the culture volume, in order to introduce a liquid into the culture volume or/and to remove liquid from said culture volume via the delivery liquid flow path, in which the at least one counter-coupling formation has a valve configuration. The valve arrangement can preferably be switched by a control configuration with a signaling means generating an electric or/and magnetic or/and electromagnetic field, the field of which acts upon a correspondingly field-sensitive counter-signaling means of the valve configuration without contact, between a blocked position, in which the valve configuration interrupts a liquid flow in the delivery liquid flow path, and an outlet position, in which the valve configuration enables a liquid flow.

As has been previously shown, the container valve configuration in the at least one counter-coupling formation can maintain the seal closure in said formation at any time at which there is no coupling contact between the counter-coupling formation of the cell culture container and the coupling formation of the liquid supply interface through pretensioning of the container valve configuration in the blocked position, such that the penetration of liquid through the counter-coupling formation into the cell culture volume and the escaping of liquid from said volume can be reliably prevented. The capacity to switch the container valve configuration enables the interruption of the delivery liquid flow path to be established and rescinded in a targeted manner, for example if the aforementioned coupling contact has been established with the liquid supply interface.

For further embodiment of the container valve configuration, express reference is hereby made to the aforementioned statements regarding the valve configuration preferred in this application, which is also applicable to the container valve configuration.

In order to prevent collisions or to make it possible to have processing at the fill or/and ventilation opening itself if the at least one counter-coupling formation is in coupling contact with the liquid supply interface, it may be advantageous for the fill or/and ventilation opening in the at least one separately formed counter-coupling formation to be provided at opposite ends of the cell culture container. This thus makes it possible to access the culture volume of one and the same cell culture container at the fill or/and ventilation opening, on one hand, and at the at least one counter-coupling formation, on the other hand, at the same time without preventing access to the other one.

The significant advantage of the present invention is that particularly advantageous economical disposable cell culture containers can be used. Therefore, the cell culture container is preferably a passive container, which is implemented apart from the at least one container valve configuration of the at least one counter-coupling formation without functional units installed in the container, i.e. permanently connected to the container, and driven by a power feed. Possible functional unit such as this are, for example, a heating mechanism or a stirring mechanism. Provided temperature control of the culture volume is necessary for maintaining the cell cultures in the cell culture container; this can be economically implemented in incubators or heating cabinets into which the cell culture container can be placed, preferably together with other cell culture containers.

Preferably, the cell culture container is stackable, which is why it has two essentially parallel end walls and jacket wall sections surrounding an end wall edge, according to a preferred further embodiment of the present invention. End walls and jacket wall sections together delineate the culture volume. It is further preferred when the end walls are the largest-area wall sections of the cell culture container, in which the jacket wall sections may form a right angle with the end walls advantageously in order to increase stacking capacity.

To ensure that a plurality of cell culture containers may be stacked in a stable manner by placing the preferably largest end walls of the directly adjacent cell culture containers next to one another, preferably the at least one counter-coupling formation, or especially preferably also the fill or/and ventilation opening, is provided in a jacket wall section. Thus, the end walls may be free of functional elements and provide maximum size and a stable stacking surface.

The further embodiments addressed in connection with the liquid supply interface or/and with the cell culture system for cell culture containers, for example the provision of two or even three counter-coupling formations, of which preferably each is provided with a container valve configuration, also apply to the cell culture container as an application subject matter by itself.

Preferably, the at least one counter-coupling formation is formed as a male coupling connecting piece, which is formed by a coupling socket of the coupling formation of the liquid supply interface radially to the exterior in the coupling contact.

The culture volume (total volume) of the cell culture container is preferably no greater than 2 L, or especially preferably no greater than 1.3 L. Thus, in the event of individual contaminated cell cultures, the total damage can be significantly limited.

BRIEF DESCRIPTION OF THE DRAWINGS

The present invention is explained in more detail in the following using the accompanying drawings. The following is shown:

FIGS. 6-14 show representations of different valve switching states (valve position configurations) of a cell culture system according to the invention with a liquid supply interface with a first to fourth connection formation and with a cell culture container according to FIGS. 1 to 3.

FIGS. 15-18 show different valve switching states (valve position configurations) of a second embodiment of a cell culture system according to the invention, in which cell culture containers are being used with three counter-coupling formations each.

FIGS. 19-21 show representations of different valve switching states (valve position configurations) of a third embodiment of a cell culture system according to the invention, which uses cell culture containers with only one single counter-coupling formation each.

DETAILED DESCRIPTION

Figure 1:
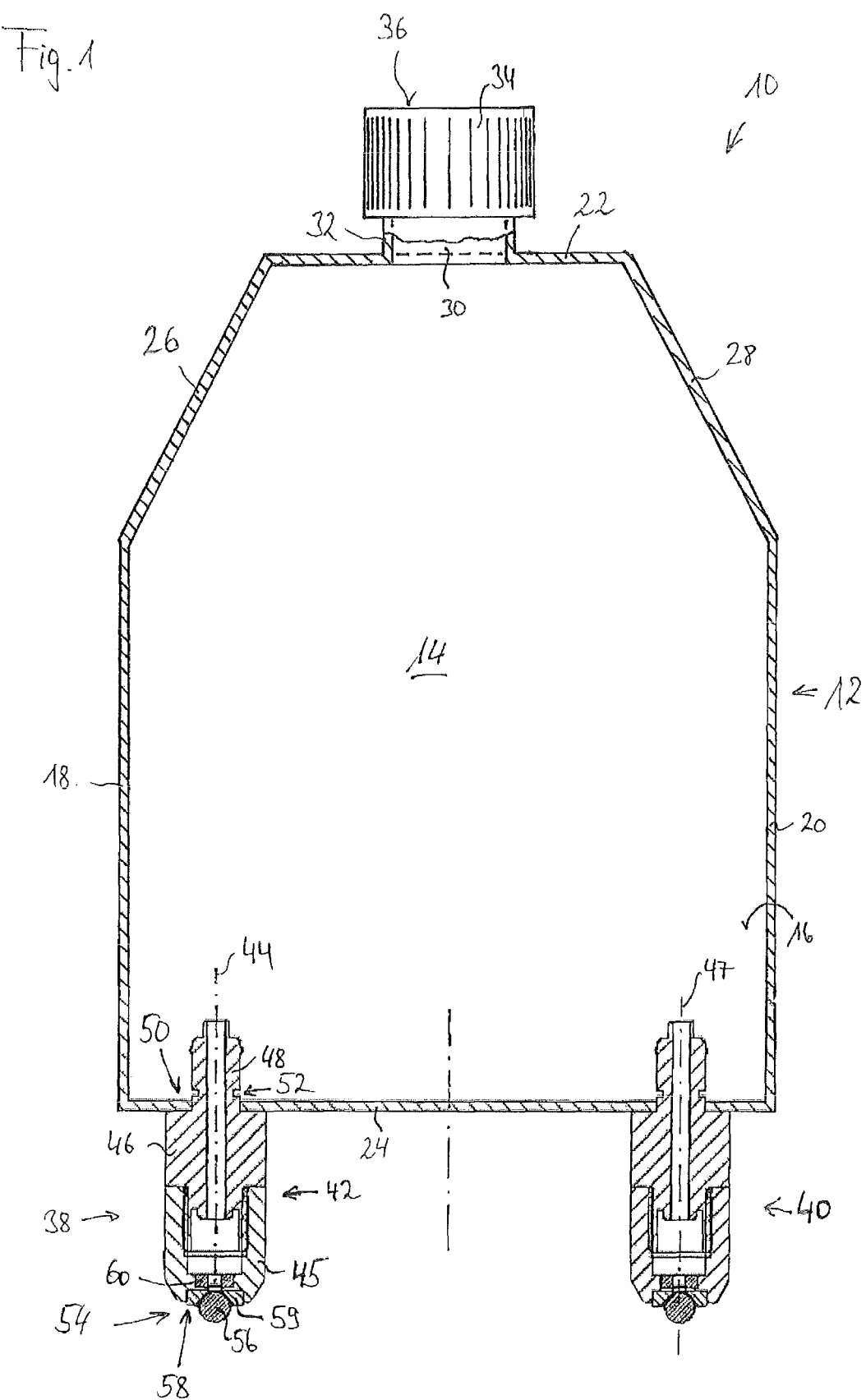
FIG. 1 shows a longitudinal sectional view through an embodiment according to the invention of a cell culture container, on which two counter-coupling formations are provided as an example.

FIG. 1 shows an exemplary embodiment according to the invention of a cell culture container generally characterized as 10. Such type of cell culture container may be used in a cell culture system according to the invention.

The cell culture container 10 has a container body 12, which encloses a culture volume 14.

The container body 12 of the cell culture container 10 preferably has two essentially parallel end walls; FIG. 1 only shows the end wall 16 to the rear of the cutting plane due to the cutting plane of this figure parallel to the end walls. Jacket wall sections, which are cut by the cutting plane in FIG. 1, are provided between the two end walls 16.

Of the jacket wall sections, the two lateral jacket wall sections, 18 and 20, are preferably parallel with respect to one another, and the front and rear jacket wall sections, 22 and 24, are parallel with respect one another. To facilitate stacking of cell culture containers 10 according to the invention, the aforementioned jacket wall sections, 20, 22, 24, preferably are adjacent and among them form a right angle. It is further preferable that each of the jacket wall sections, 18 to 24, form a right angle with the parallel end walls.

However, this does not rule out the possibility that the jacket wall sections also have jacket wall sections, 26 and 28, that preferably form a right angle with the end walls but not with their adjacent jacket wall sections 18 and 22 or 20 and 22. For example, these jacket wall sections, 26 and 28, may extend tilted toward the front jacket wall section 22 such that the container body 10 tapers toward the front wall section 22.

The container body 10 has an access opening 30, which may be used as a fill or/and ventilation opening for filling or emptying the culture volume 14 or for the ventilation thereof. Preferably, the access opening 30 is formed at an access neck 32, which can be optionally closed or opened by a closure cover 34. The closure cover 34 may be formed as a threaded cap with an internal thread for better retention at the access neck 32, with the internal thread having an outer thread preferably provided at the exterior of the access neck 32, which can be screwed on in a known manner. If there is ventilation of the culture volume 14, i.e. an exchange of gas between the culture volume 14 and the outer environment of the cell culture container 10, even when an otherwise closed access opening 30 is desired, the closure cover 34 may have one or more breach openings in its front case 36 oriented orthogonally with respect to the drawing plane in FIG. 1 in the example, through which gas may be able to pass into the culture volume 14 and flow back out of it, but the dimensions of which are selected such that typical laboratory devices cannot pass through them.

Preferably, the cell culture container 10 is an economical disposable cell culture container without the electrically driven heating mechanism formed thereon and without the electrically driven stirring mechanism provided thereon. For better monitoring and observing of the cell culture process, the container body 12 is preferably formed at least in sections, or preferably completely, of optically transparent plastic, for example made of polymethyl methacrylate (PMMA) or another suitable transparent plastic, depending on the desired chemical resistance, as a function of the expected chemical or biochemical materials, that are on the inside of the culture volume 14 according to the operation.

The cell culture container 10 further has one or more counter-coupling formations 38, in precisely two counter-coupling formations, 38 and 40, in the example shown in FIG. 1.

The cell culture container 10 may have any number of counter-coupling formations considered by themselves, in which even the number of three counter-coupling formations provides separate delivery liquid flow paths for filling, emptying, and for random sampling of the culture volume 14 or from the culture volume 14. If a third counter-culture formation is desired in the embodiment of a cell culture container 10 shown in FIG. 1, this can be arranged in the center between counter-coupling formations 38 and 40 that are indicated, as shown by the dash/dotted line of the delivery liquid flow path of said third counter-coupling formation.

In the event only one single counter-coupling formation is desired, it can be provided at any of the three places shown in FIG. 1, or even at any of the other places in a different jacket wall section or even in an end wall.

The stacking capacity of the cell culture containers 10 by placing them one on top of the other at their end walls is, however, facilitated in an advantageous manner in that both the access opening 30 as well as all of the counter-coupling formations, 38 and 40, are provided at jacket wall sections. The accessibility of the counter-coupling formations, 38 and 40, on one hand, as well as the access opening 30, on the other hand, independently of one another can be improved even more in that, as shown in FIG. 1, counter-coupling formations 38 and 40 and the access opening 30 are formed at different jacket wall sections, 22 and 24, which are preferably opposite one another. In this case, even access openings 30 can be accessed by an operator at cell culture containers 10 stacked on top of one another and next to one another on one side of the stack wall, and the counter-coupling formations, 38 and 40, can be accessible through a liquid supply interface, described in more detail below, on the opposite side of the stack wall.

The counter-coupling formations, 38 and 40, are formed preferably identically to facilitate production and assembly, which means that only one counter-coupling formation is described representatively for all counter-coupling formations provided on the cell culture container 10 in the following.

The counter-coupling formation 38 has a counter-coupling formation housing 42, which may be formed as a single piece, or in multiple pieces as shown in FIG. 1. The housing 42 defines a first delivery liquid flow path 44, which extends between the outer environment of the cell culture container 10 and its culture volume through the first counter-coupling formation 38.

The counter-coupling formation housing 42 may have a housing access component 45 further away from the cell culture container 10, which may be permanently connected to the housing support component 46, which is closer to the cell culture container 10. This connection may, for example, be a threaded connection, particularly in that the housing access component 45 is screwed onto a threaded shaft of the housing support component 46.

Preferably, the housing support component 46 is used for fastening the first counter-coupling formation 38 onto the cell culture container 10, for example in that a fastening shaft 48 of the housing support component 46 penetrates an allocated opening 50 in a wall of the cell culture container 10. The fastening shaft 48 may be affixed with the known fastening means in the particular wall of the cell culture container 10, for example by means of mechanical fastening and sealing means 1, which are not shown in more detail in FIG. 1, but which, however, are commonly known to the average person skilled in the art, inserted into a circumferential groove 52. In addition or as an alternative to this, the counter-coupling formation housing 42 may be bonded or/and welded to the container body 12.

Preferably, the counter-coupling formations, 38 and 40, are provided at a jacket wall section, particularly at a jacket section 22 having the access opening 30, which is diametrically opposed to jacket wall section 24.

The first counter-coupling formation 30 may further have a container valve configuration 54, which can be switched between a blocked position and an outlet position. The container valve configuration 54 of the first counter-coupling formation 38 is shown in its blocked position in FIG. 1, in which it interrupts the delivery liquid flow path 44. In its outlet position, which is not shown in FIG. 1, the container valve configuration 54 enables a liquid flow along the delivery liquid flow path.

Even though the container valve configuration 54 may be completely surrounded by the housing 42 of the first counter-coupling formation, with the exception of the delivery liquid flow path 44, it is preferably provided at the access-side longitudinal end area of the first counter-coupling formation 38. This facilitates its cleaning when the liquid supply interface is coupled, which is described in the following.

The container valve configuration 54 has a valve body 56, which is positioned on a valve seat 58 with a negative-conical contact surface, in the blocked position shown in FIG. 1. For reasons of improved sealing capacity, the valve seat 58 preferably has a contact component made of a material, which deforms slightly under the pretensioning force acting in the blocked position in the container valve configuration 54. Suitable material includes, for example, an elastomer plastic material such as silicone, rubber, or a liquid-impermeable, closed-cell plastic, such as PU foam, or the like.

The valve body 56 is preferably formed as a sphere for reasons of symmetry, so that, for its function, it does not reach its orientation relative to the valve seat 58.

The valve seat preferably has a tension component 60, which in the present case is formed as a permanent magnet, on the side of the contact component 59 facing away from the valve body 56. The permanent magnetic tension component 60 is preferably formed in the shape of a ring and is penetrated by the allocated delivery liquid flow path 44, just as the contact component 59.

As described in more detail below in connection with FIGS. 4 and 5, the contact component 59 not only serves as a sealing contact of the valve body 56, but also is a sealing contact at a counter-sealing surface of the liquid supply interface, which is formed to establish a liquid-transferring coupling contact with the counter-coupling formations, 38 and 40, provided at the cell culture container 10.

Figure 2:
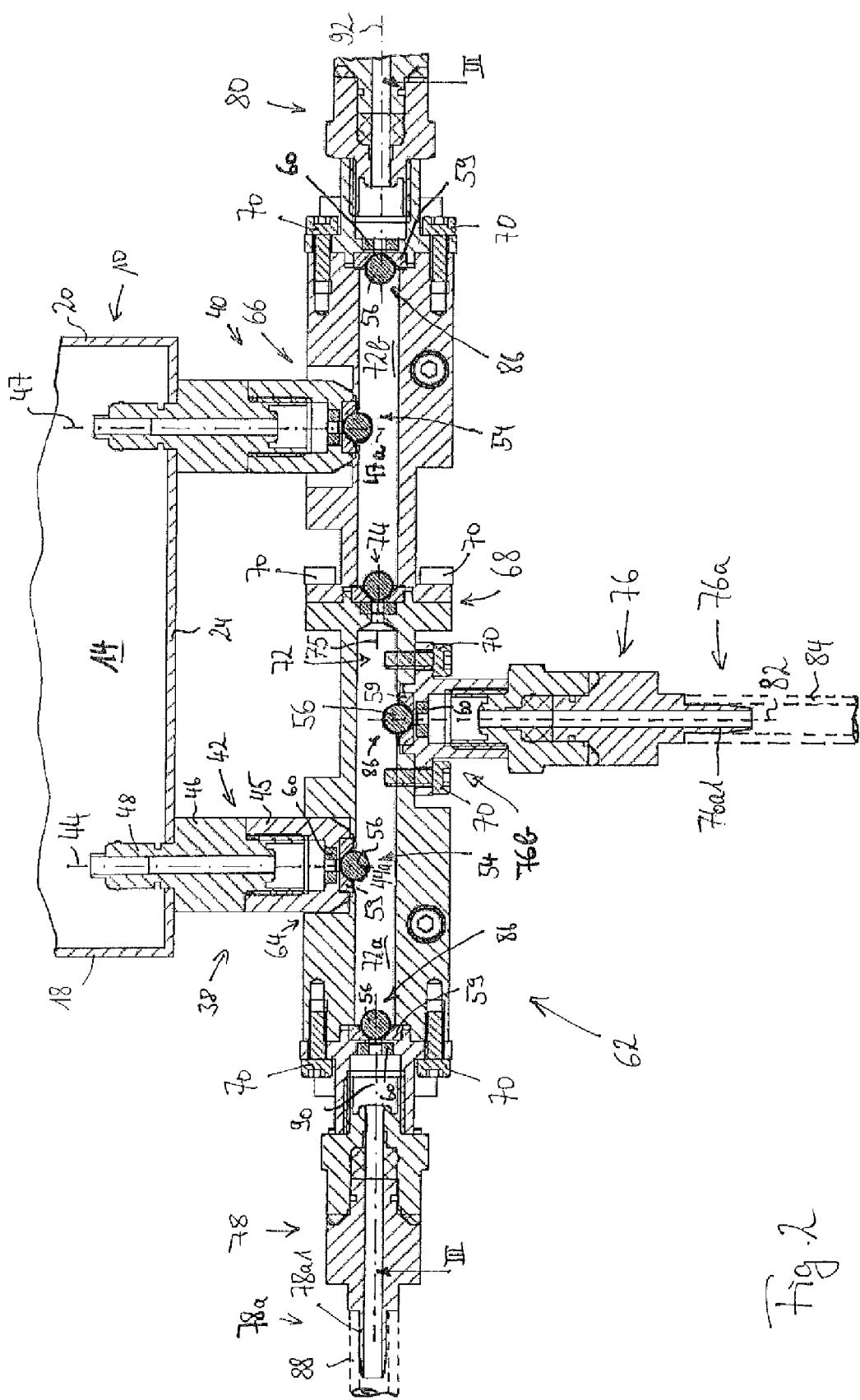
FIG. 2 shows a sectional view through an exemplary embodiment according to the invention of a liquid supply interface, which is in liquid-transferring contact with the cell culture container from FIG. 1.

FIG. 2 shows the longitudinal end of the cell culture container 10 shown in FIG. 1 on the counter-coupling formation side, which is in liquid-transferring coupling contact with a liquid supply interface 62 via its counter-coupling formations, 38 to 40.

In the example shown in FIG. 2, the liquid supply interface 62 has a first coupling formation 64, which is in coupling contact with the first counter-coupling formation 38 and has a second coupling formation 66, which is in liquid-transferring coupling contact with the second counter-coupling formation 40. The first and the second coupling formation, 64 and/or 66, are preferably formed as sockets in the housing 68 of the liquid supply interface 62.

When only one container valve configuration 54 is provided on the cell-culture-container side at the coupling point of the coupling formation and the counter-coupling formation, the housing 68 of the liquid supply interface 62 has exactly the same number of coupling formations as the cell culture container 10 to be coupled has counter-coupling formations. Accordingly, the liquid supply interface 62 may have only one or even three or more coupling formations.

The housing 68 of the liquid supply interface 62 is advantageously constructed in multiple pieces. However, this is not mandatory. If the housing comprises multiple pieces, it is preferable if separating surfaces are placed between the individual housing parts orthogonally with respect to a liquid flow path formed at the respective housing part and are penetrated by the liquid flow path. The individual housing parts are attached to one another using screws 70 in the example shown. As an alternative or in addition to the threaded connection, individual or all housing parts connected to one another may be welded or/and bonded to one another.

The housing 68 initially defines a flow area 72, which is divided into two sub-flow areas, 72a and 72b, by a separating valve configuration 74, with the two sub-flow areas situated on both sides of the separating valve configuration 74. A connecting flow path 75 proceeding between the two coupling formations, 64 and 66, extends through the separating valve configuration 74 in the example shown.

Advantageously, both sub-flow areas, 72a and 72b, are formed circular-cylindrically except for the start, end, and intermediate feeds, which significantly facilitates cleaning in the CIP process or in the SIP process as explained below.

The coupling formations, 64 and 66, are shown as formed with different diameters in the example shown in FIG. 2 in order to indicate that, even with coupling contact established between the coupling formation and the counter-coupling formation, it is advantageous when a section of a formation comprising the coupling formation and the counter-coupling formation surrounds an axial section of the respective other formation radially on the exterior, but the two formations do not necessarily have to make contact with one another in the area of this encompassing section. The larger clear width of the second coupling formation 66 as compared to the outer diameter of the second counter-coupling formation 40 facilitates the establishment of the coupling contact between the coupling formation 66 and the counter-coupling 40 significantly without fearing that the seal will be compromised. It is important in this case that the liquid supply interface 62 be routed at a corresponding movement device sufficiently precisely in order to establish coupling contact.

The embodiment of the liquid supply interface 62 shown as an example in FIG. 2 has a first connection formation 76, a second connection formation 78, and a third connection formation 80. The first connection of formation 76 defines a first liquid flow path 82, which extends between the flow area 72, which is more precisely the sub-flow area 72*a* in the present example, and the first connection formation 76, and furthermore into the first connection formation 76.

At its longitudinal end 76*a* positioned away from the flow area 72, the connection formation 76 is formed, for example, by an adapter piece 76*a*1, in order to connect with a fluid line 84, which, in the example shown in FIG. 2, preferably leads to a nutrient medium reservoir, which is not shown in FIG. 2 (see FIG. 6*ff.*). The fluid line 84 is preferably a flexible fluid line, for example made of an elastomer hose, which is placed onto the adapter piece 76*a*1 and there can be secured against undesirable removal with securing means in a known manner, for example a hose clamp.

Nutrient medium can be introduced into the flow area 72 and then distributed out from there through the fluid line 84, i.e. along the first liquid flow path 82. For example, fresh nutrient medium can be introduced into the culture volume 14 of the cell culture container 10 along the delivery flow path 44, via the first coupling formation 64 and the first counter-coupling formation 38.

The fluid line 84 may also be formed as a rigid pipeline, but this is less preferred, because the nutrient medium reservoir must also be moved along with the liquid supply interface 62.

In the coupled state shown in FIG. 2, that particular part of the delivery liquid flow path 44 that extends into the flow area 72 in the area of the first coupling formation 64 is identical to a coupling flow path 44*a* that extends between the flow area 72 in the first coupling formation 64. When liquid-transferring coupling contact is established between the first counter-coupling formation 38 and the coupling formation 64, the first coupling flow path 44*a* merges from the flow area 72 into the delivery flow path 44. These flow paths are then collinear. The same thing applies to the second delivery liquid flow path 47 of the second counter-coupling formation 40 and the second counter-coupling path 47*a* of the second coupling formation 66.

The first connection formation 76 may be formed in multiple pieces, as is shown in FIG. 2. A multi-piece formation supports in this case the assembly and subsequent maintenance of the liquid supply interface 62.

The first connection formation 76 has a valve configuration 86 at the longitudinal end 76*b*, of the first connection formation 76, closer to the flow area 72. The valve configuration 86 is constructed identically to the container valve configuration 54 of the first and the second counter-coupling formation, 38 and/or 40, which means that similar and functionally similar components and component sections have been given the same reference characters as those for container valve configuration 54 at valve configuration 86. Otherwise, in order to describe valve configuration 86, express reference is made to the description of the container valve configuration 54 indicated in the present application, which also applies not only to the first connection formation 76 but also the other connection formations, 78 and 80, for valve configuration 86.

Figure 3:
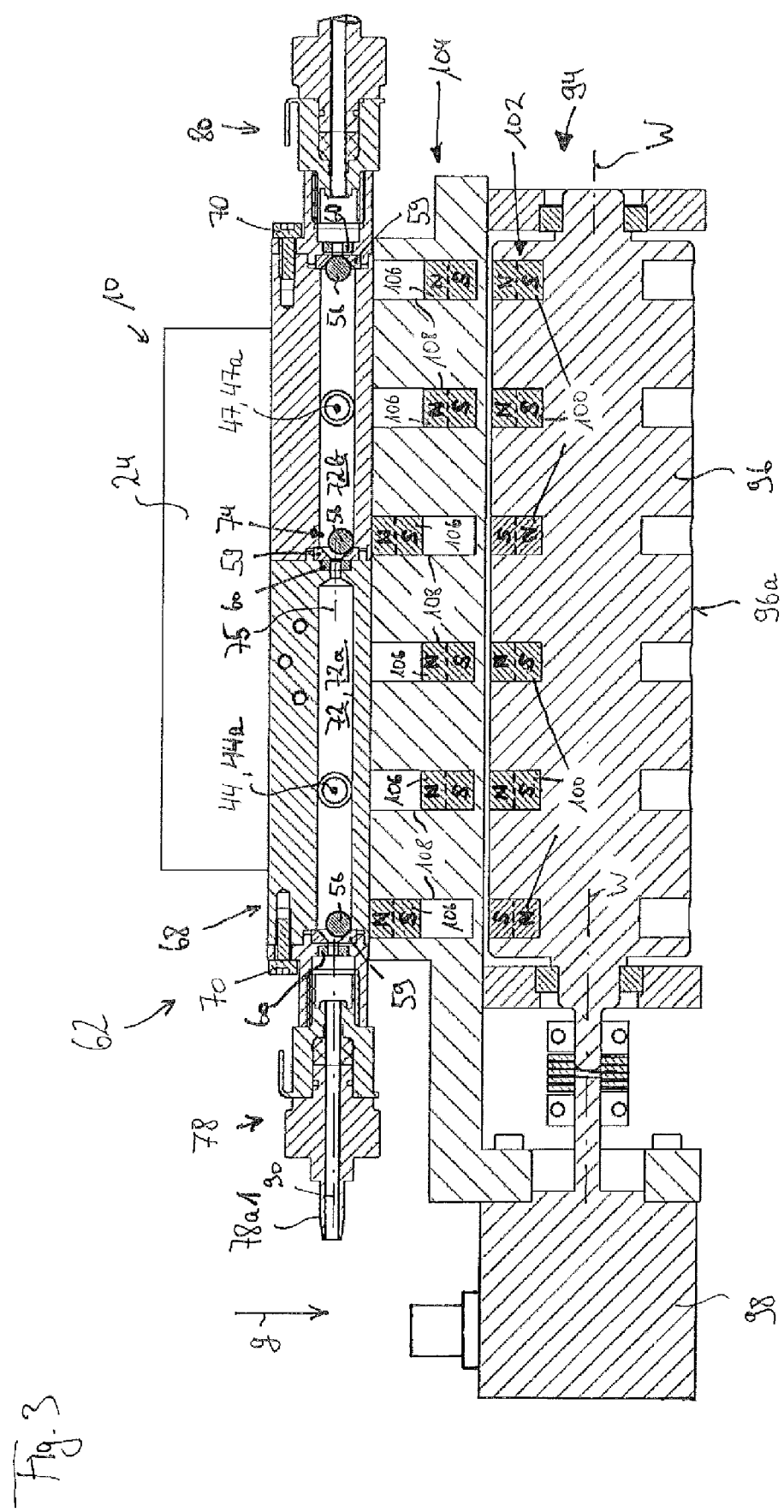
FIG. 3 shows a longitudinal sectional view of the liquid supply interface and of the cell culture container in section plane III-III of FIG. 2 with a control configuration, which has a placement configuration provided between signaling means and the liquid supply interface.

Due to the preferred permanent fastening shown in FIG. 2 of the connection formation 76 at the housing part, directly defining the flow area 72, of the liquid supply interface 62 by means of the screws 70—which moreover do not penetrate into the flow area 72 contrary to what is shown in FIG. 2, but rather lie in front of the drawing plane in FIG. 2 as can be seen in FIG. 3—the valve arrangement 86 of the first connection formation 76 is completely surrounded by the housing 68 with the exception of the first liquid flow path 82.

The valve body 56 is preferably a sphere made of ferromagnetic material, which is pretensioned in its blocked setting against the elastically deformable contact component 59 of the valve seat 58, by the permanent-magnetic tension component 60.

The second and the third connection formation, 78 and/or 80, are each formed identically to the first connection formation 76, such that reference is expressly made to the description of the first connection formation for the description thereof.

Preferably, an adapter piece 78*a*1 provided at the longitudinal end 78*a* away from the flow area is connected to a second fluid line 88, which is connected to a cleaning fluid reservoir, which is not shown in FIG. 2, on the other end. A second liquid flow path 90 further extending between the flow area 72, shown more precisely as sub-flow area 72*a* in FIG. 2, and the second connection formation 78 enables, in the exemplary embodiment shown in FIG. 2, i.e. preferably an introducing of cleaning fluid from the cleaning fluid reservoir, not shown, into the flow area 72, which is more precisely into sub-flow area 72*a*. Thus, a maximum length of the flow area 72 is accessible by the cleaning fluid, and preferably the second connection formation 78 is provided at an axial longitudinal end of the flow area 72.

The third connection formation 80 is preferably connected to a discharge, which is not shown in FIG. 2. This can be done through a fluid line (not shown in FIG. 2) mounted onto the third connection formation 80 in the manner previously described with reference to the first and the second connection formation, 76 and 78, respectively.

A third liquid flow path 92, through which liquid in the liquid flow area 72 can be removed from said area and routed to a discharge, furthermore extends between the liquid flow area 72, more precisely between sub-flow area 72*b* as indicated in FIG. 2, and the third connection formation 80.

In order to route cleaning fluid introduced into the flow area 72 through the second liquid flow path 90 via the longest section of the liquid flow area of 72 possible and thus in order to clean the largest section of the liquid flow area 72 possible, it is preferable for the third connection formation 80 to be arranged at the longitudinal end of the flow area 72 opposite the assembly point of the second connection formation 78. Thus, cleaning fluid introduced through the second connection formation 78 into the flow area 72 cannot be removed from said area via the third connection formation 80 until it has passed through essentially the entire flow area 72. Thus, the flow area 72 can essentially be flushed with cleaning fluid over its entire length via the second and third connection formation, 78 and 80, respectively.

To ensure that the entire liquid supply interface 62 including the counter-coupling formations, 38 and 40, currently in coupling contact with said interface can be cleaned as efficiently as possible with such type of cleaning process before the culture volume 14 of the respectively coupled cell culture container 10 has fresh nutrient medium routed to it or existing nutrient medium is drained from it, all feed points of a further connection formation or of a coupling formation in the flow area 72 are preferably located between the second connection formation 78 and the third connection formation 80, so that they are positioned along the aforementioned flushing path and can be reached by cleaning fluid flowing from the second connection formation 78 to the third connection formation 80.

In order to clean the valve bodies 56 of the valve configurations 86 and the container valve configurations 54 as well as the separating valve configuration 74 as efficiently as possible, they penetrate either into the flow area 72 or are located completely within it. The valve bodies 56 preferably penetrate into the flow area 72 with at least more than half of their body volume.

FIG. 3 shows the arrangement shown in FIG. 2, characterized by arrow III-Ill, in the orthogonal cutting plane with respect to the drawing plane from FIG. 2. In this case, FIG. 3 shows a control configuration 94, which is preferably arranged under the assembly comprising the liquid supply interface 62 and the cell culture container 10 coupled thereto. The position of the second valve configuration 86 in the second connection formation 78 and the valve position of the separating valve configuration 74 differ in FIG. 3 from those in FIG. 24 purposes of explanation.

The control configuration 94 may have a roller 96 rotating around a roller axis W, which may be driven by a drive 98, for example an electric motor drive for rotating around the roller axis W.

A plurality of signaling means 100 may be arranged around the periphery of the jacket surface 96a of the roller 96, which are formed by permanent magnets in the present example. These permanent magnets are preferably oriented such that their N-S polarization direction corresponds to a radial direction starting from the roller axis W.

In doing so, the liquid supply interface 62 in coupling contact with a cell culture container 10, that is part of the signaling means 100, is combined into a set 102 of signaling means for a concrete valve positioning configuration of the valve configurations 54, 74, and 86. Thus, the row of six signaling means 100 placed above the roller axis W positioned in the cutting plane in FIG. 3 forms such type of set.

Diametrically opposed to this is another set of signaling means, which, however, is not indicated in FIG. 3. Instead of this, only the collection areas provided for the signaling means are shown in the roller 96. Between said areas, additional sets of signaling means may be provided along the periphery of the roller 96.

The placement configuration 104 may be provided between the liquid valve interface 62 and the cell culture container in coupling contact with it, on one hand, and the roller 96, on the other hand, in order to enable even more chronologically precise switching of the valve configurations 54, 74, and 86.

As in a set 102 of signaling means 100 of the roller 96, it is also preferable in the placement configuration for every switchable valve configuration 54, 74, 86 of a valve position configuration to have precisely one permanent magnet 106. Each permanent magnet 106 in this case is placed so as to shift, in a channel 108, along said channel 108, so as to shift between a position closer to the roller and a position closer to the valve configuration.

The permanent magnets 106 in this case are selected such that the magnetic field starting from them and acting upon the valve body 56 is stronger, at least in the position closer to the valve configuration, than the magnetic field starting from the magnetic tension components 60 and acting upon the respective valve body 56. In addition, the magnets 106 are preferably arranged polarized along their shifting axis, designed such that one pole, for example the north pole, references the respectively allocated valve configuration, and the respective other pole, for example the south pole, references the roller 96.

The placement configuration 104 is preferably arranged such that the permanent magnets 106 are pretensioned in their position closer to the roller in the respective channels 108 by the force of gravity indicated by the arrow g, in which, for example, permanent magnet nos. 2, 3, 5, 6 (when counting from left to right) are located in FIG. 3.

With the corresponding placement of the signaling means 100, the permanent magnets 106 are shifted from their position closer to the roller to their position closer to the valve configuration, for example by placing like poles opposite one another, i.e. repellent poles of permanent magnets 106 and signaling means 100, with the approximation of said signaling means 100 to the permanent magnets 106 of the placement configuration 104 by the magnetic fields starting from the signaling means 100. By placing like poles, i.e. poles that attract one another, of permanent magnets 106 and signaling means 100 opposite one another, the permanent magnets 106 are magnetically held in the position closer to the roller, in addition to the constantly acting force of gravity.

Upon approximation of a magnet 106 of the placement configuration 104 at the valve configuration allocated to it, the valve body 56 of same is more strongly pulled by the permanent magnet 106 located in its position closer to the valve configuration than by the tension component 60 of the respective valve configuration. The valve body 56 thus moves from its blocked position, in which it has contact with the contact component 59 to form a seal of a passageway opening through the valve configuration, in a position in which a passageway is possible through the respective valve configuration, and thus a flow is enabled along the valve flow path allocated to the valve configuration.

With the example shown in FIG. 3, the valve body 56 of the valve configuration 86 of the second connection formation is removed from its valve seat 58, particularly from the contact component 59, by the control configuration 94, such that the second liquid flow path 90 is exposed to the flow of a liquid, which in this case is cleaning fluid.

The separating valve configuration 74 is likewise adjusted in its outlet position by the control mechanism 94 in the position shown in FIG. 3, because its valve body 56 is also shifted away from the contact component 59 toward the allocated fourth permanent magnet of the placement configuration 104. Thus, in addition to the second liquid flow path, the connection flow path 75 extending between the first coupling flow path 44a and the second coupling flow path 47a is also exposed for the flow of liquid.

In the present example, there is a 1:1 allocation between the signaling means 100 and the valve configurations, 54, 74, and 86, which are available at a liquid supply interface 62 coupled to a cell culture container 10. There is also such type of 1:1 allocation between the magnets 106 of the placement configuration 104 and the existing valve configurations. The signaling means 100 and the permanent magnets 106 arranged all the way to the left in FIG. 3 are allocated to the second valve configuration 86 in the second connection formation 78. Their neighbors to the right, as signaling means 100 or permanent magnet 106, are allocated to the first container valve arrangement 54 at the first counter-coupling formation 38. Their respective neighbors to the right in FIG. 3 are allocated to the first valve configuration 86 of the first connection formation 76. Their neighbors to the right are allocated to the separating valve configuration 74. Their neighbors to the right are allocated to the second container valve configuration 54 of the second counter-coupling formation 40, and the combination comprising signaling means 100 and permanent magnet 106 all the way to the right in FIG. 3 is allocated to the third valve configuration 86 of the third connection formation 80.

The sets 102 of signaling means 100 distributed around the periphery of the jacket surface 96a of the roller 96 have signaling means 100, each of which are arranged differently in their polarization, in order to adjust the valve position configuration, allocated to the respective signaling means set 102, of all six involved valve configurations, 54, 74, and 86, by approximation of the respective set 102 of signaling means 100 to the placement configuration 104.

The position of valve configurations 54, 74, and 86 shown in FIG. 3 is only exemplary in nature and not assigned any concrete function.

Figure 4:
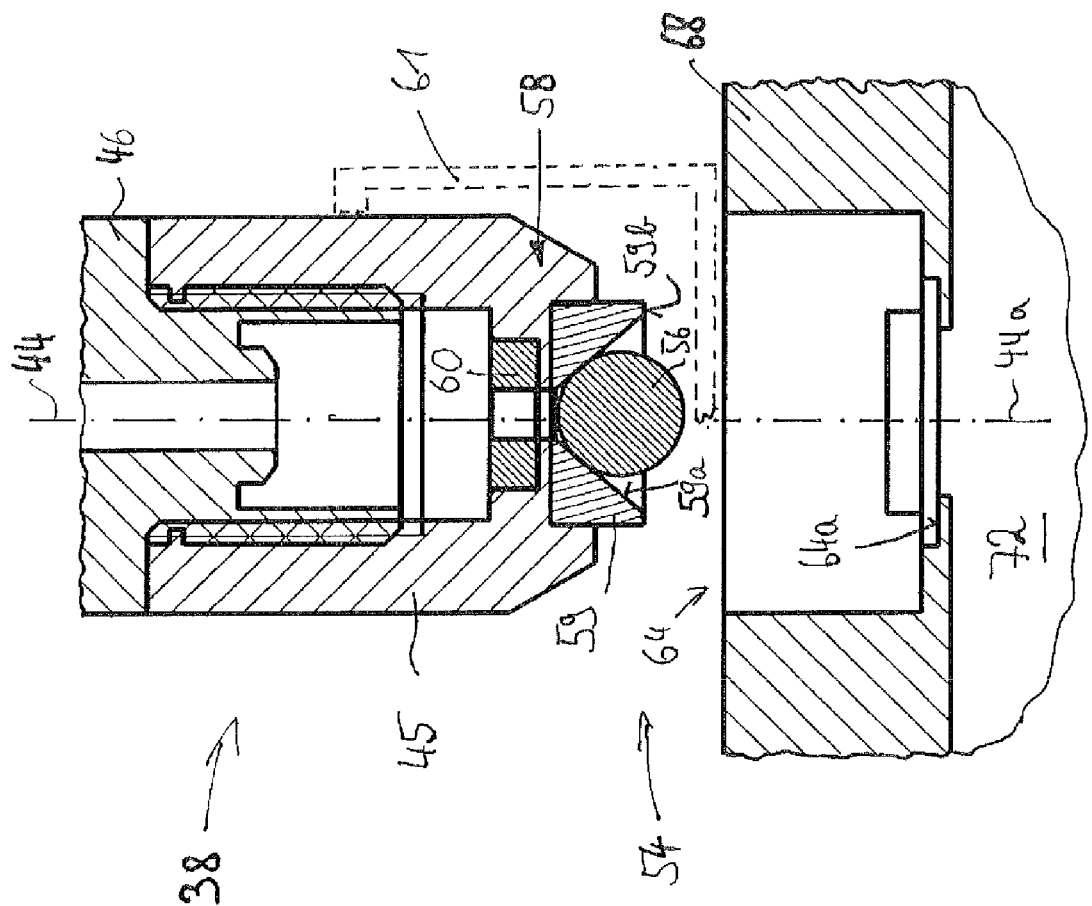
FIG. 4 shows a detailed view of a coupling formation of the liquid supply interface from FIG. 2 and a counter-coupling formation of the cell culture container of FIGS. 1 to 3 in a state in which no coupling contact has been established between them.
Figure 5:
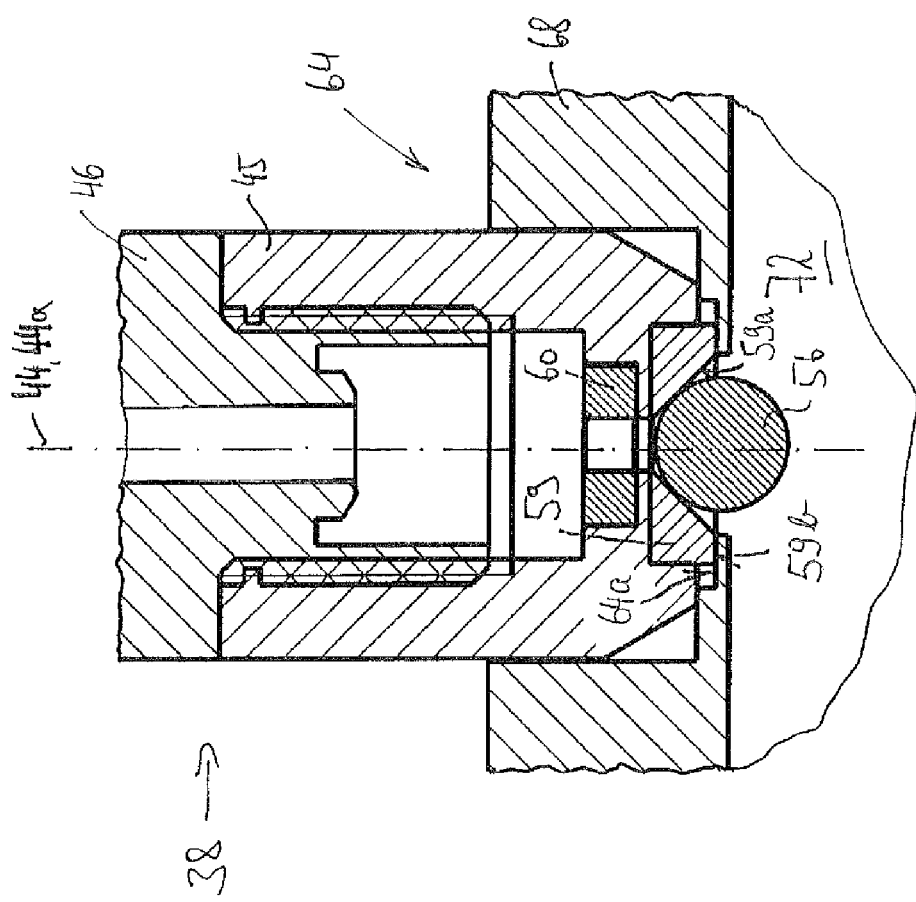
FIG. 5 shows the components from FIG. 4 with liquid-transferring coupling contact established between them.

FIGS. 4 and 5 show an example of how the contact component 59 of the valve configurations 54 shown in the present embodiment are used to seal the coupling point between the first coupling formation 64 on the supply interface side and the counter-coupling formation 38 on the cell culture container side. The principal demonstrated here also applies, however, to the coupling comprising the second coupling formation 66 and second counter-coupling formation 40 and would also apply at the coupling point of a potential third coupling formation and third counter-coupling formation.

In a similar manner, the separating surfaces extending in a longitudinal end away from the tension component advantageously constrained by the assembly between individual components of the housing 68 of the liquid supply interface 62 according to the principle shown in FIGS. 4 and 5 is sealed off by the deforming contact of the contact component 59 at a counter-sealing surface of another housing component.

FIG. 4 shows the first counter-coupling formation 38 not in contact with the allocated first coupling formation 66, which means that while the valve body 56 forms a sealing contact at the negative-conical contact surface 59a of the contact component 59—based on the magnetic tensioning force starting from the tension component 60—the content component 59 is otherwise essentially not deformed. The contact component 59 has a surrounding face ring surface 59b at its longitudinal end away from the tension component. In the example shown, this ring surface 59b is oriented orthogonally with respect to the drawing plane in FIG. 4. In this state, the counter-coupling formation can be covered by a push-on cover 61, shown on one side and indicated by the dashed line, and protected from contamination.

The coupling formation 36 has a counter-sealing surface 64a, which is formed, when a liquid-transferring coupling contact is established between the first coupling formation 64 and the first counter-coupling formation 38, to attain contact with the annular-shaped end face (face ring surface) 59b of the contact component 59.

FIG. 5 shows the first coupling formation 64 and the first counter-coupling formation of 38 when the coupling contact is established, as can also be seen in FIG. 2.

There it can be seen how the longitudinal end, further away from the tension component, of the contact component 59 with its face ring surface 59b is attained, with deformation, in contact with the counter sealing surface 64a of the housing component, having the first coupling formation 64, of the housing 68 of the liquid supply interface 62. The coupling point and particularly the coupling flow path 44a and the delivery liquid flow path 44 are sealed off radially to the outside against undesirable escaping of liquid through this deforming contact. The same thing applies to any undesirable inlet of liquid into these liquid flow paths.

This previous description in FIGS. 4 and 5 applies to the radial seal of all valve configurations shown in the embodiment discussed here.

FIGS. 6 to 14 show by means of diagrams an example operating process of a cell culture system with cell culture containers 10 according to FIG. 1 and with a modified liquid supply interface 62', which has a fourth connection formation, contrary to the liquid supply interface 62 shown in FIGS. 2 and 3. The fourth connection formation is identified as 110 in FIGS. 6 to 14 (as well as FIGS. 15 to 21). It also has a valve configuration 86. The fourth liquid flow path, which proceeds from the flow area 72 through the fourth valve configuration 86 of the fourth connection formation 10 and beyond, has the reference character 112.

The cleaning fluid reservoir is identified as 114. The nutrient medium reservoir has the reference character 116. A disposal container connected to the third connection formation 80 is identified as 118. The sampling container 120, in which samples removed from the respectively connected cell culture container 110 are collected, is connected to the fourth connection formation 110.

Delivery pumps 122, which are of no further interest and which ensure the delivery of liquids into the fluid lines connected to them in the respectively desired conveying direction, are provided between the respective first to fourth connection formations 76, 78, 80, and 110 and the reservoirs or containers 114, 116, 118, and 120 connected to them via fluid lines.

Figure 6:
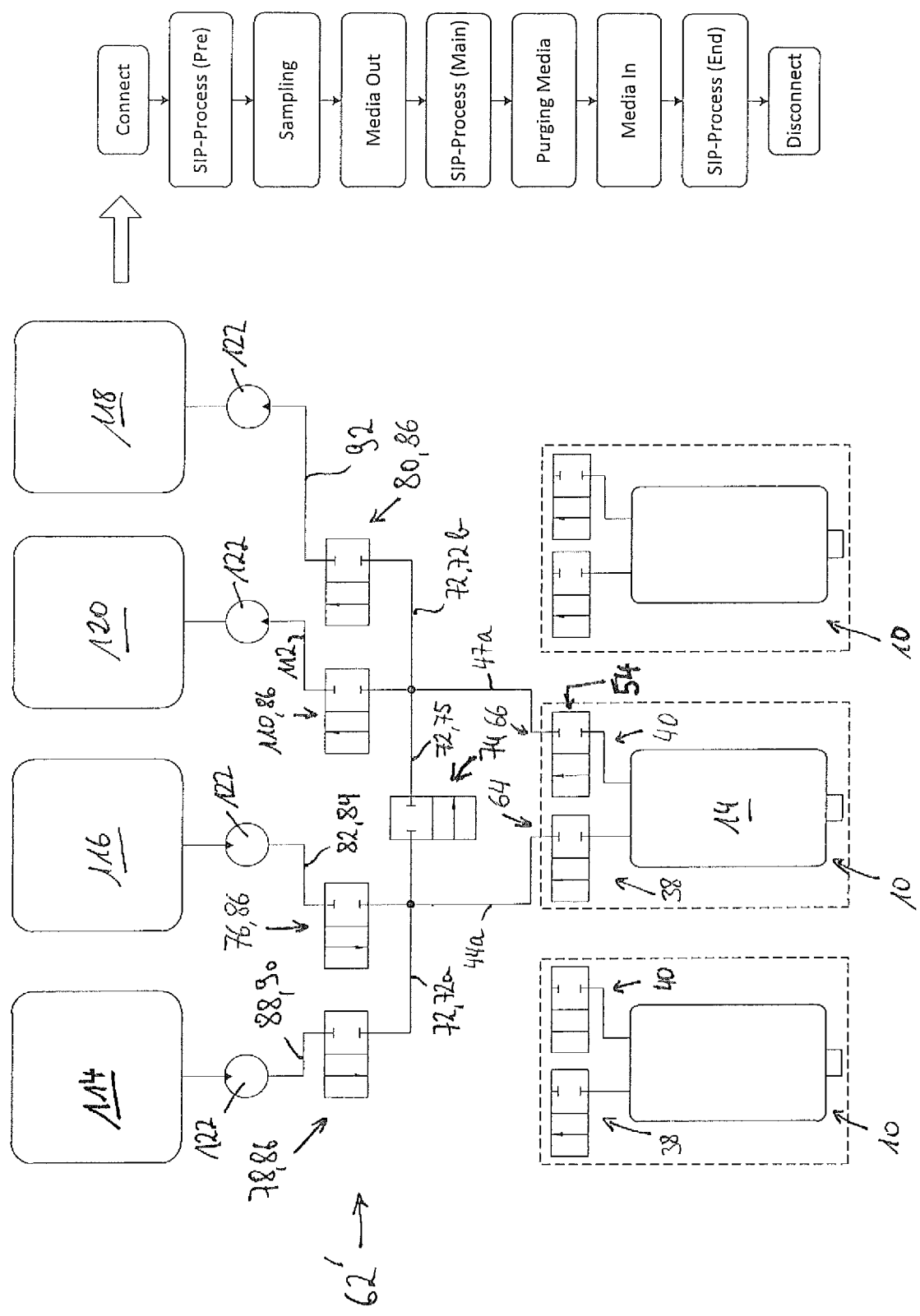

FIG. 6 shows a basic valve position configuration, as is present when a liquid-transferring coupling contact is established between the first and the second coupling formation, 64 and 66, and the first and the second counter-coupling formation, 38 and 40, respectively. All existing valve configurations, 54, 74 and 86 in this case are in their blocked position in order to prevent any undesirable flow of liquid.

Figure 7:
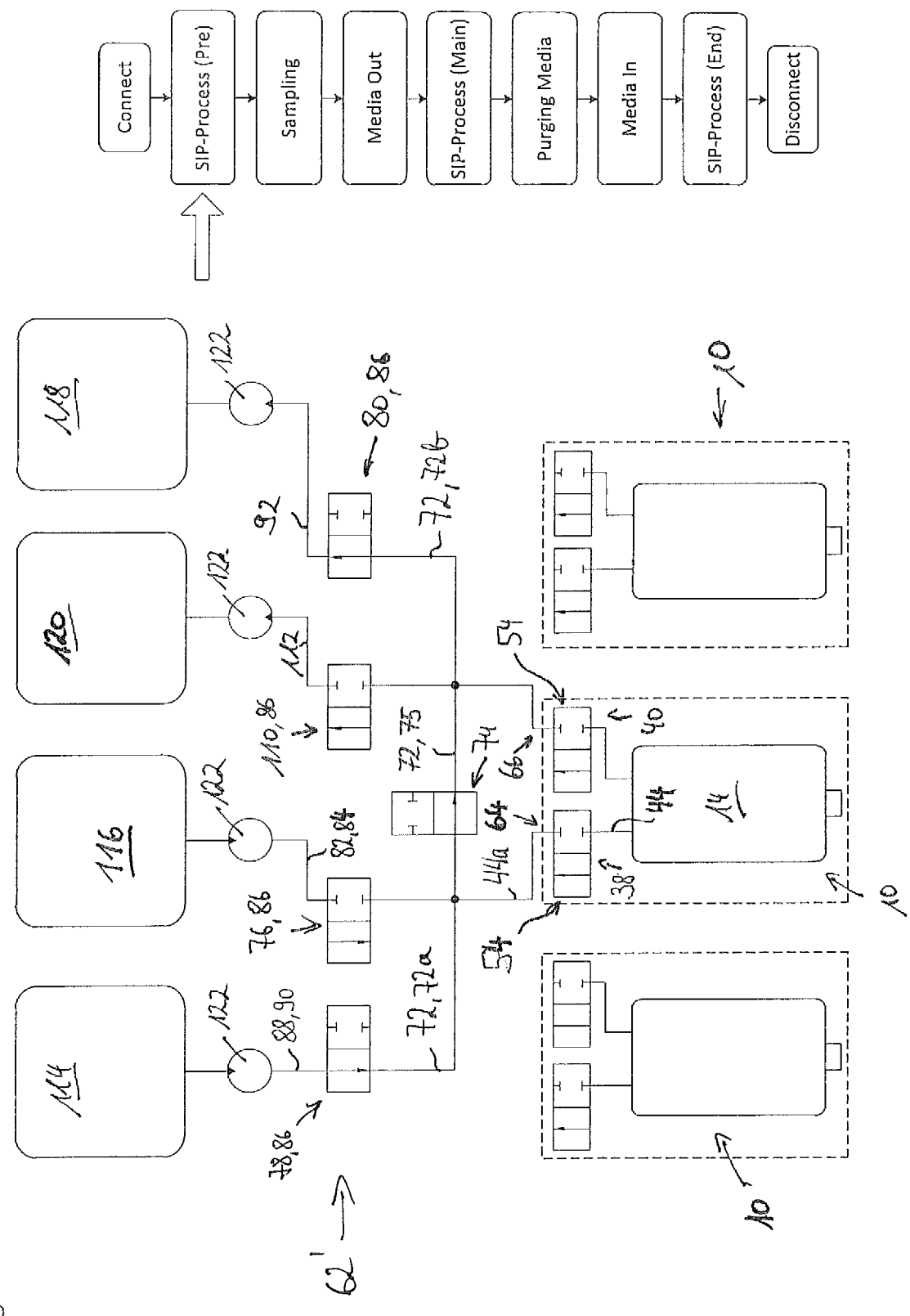

FIG. 7 shows an SIP process, which is preferably after the establishment of the coupling contact, with which a predetermined cleaning condition is established at the container valve configurations 54 and in the liquid supply interface 62'. To this end, the separating valve configuration 74 and the valve configurations 86 of the second and of the third connection formation, 78 and 80 respectively, are switched to their outlet position. By means of the pump 112 coupled to the cleaning fluid reservoir 114, cleaning fluid is removed from the reservoir 114 and routed through the second connection formation 78 into the flow area 72; it continues further through this area and is pumped through the third connection formation 80, optionally with the support of the delivery pump 122 connected to the liquid flow path 92 in the disposal container 118. Due to the penetration of the valve body 56 into the flow area 72 flushed with cleaning fluid, the valve configurations 54, 74, and 86 involved are also cleaned, which establishes a cleanliness condition, which prevents cross-contamination between cell culture containers 10 that are coupled at different times.

Figure 8:
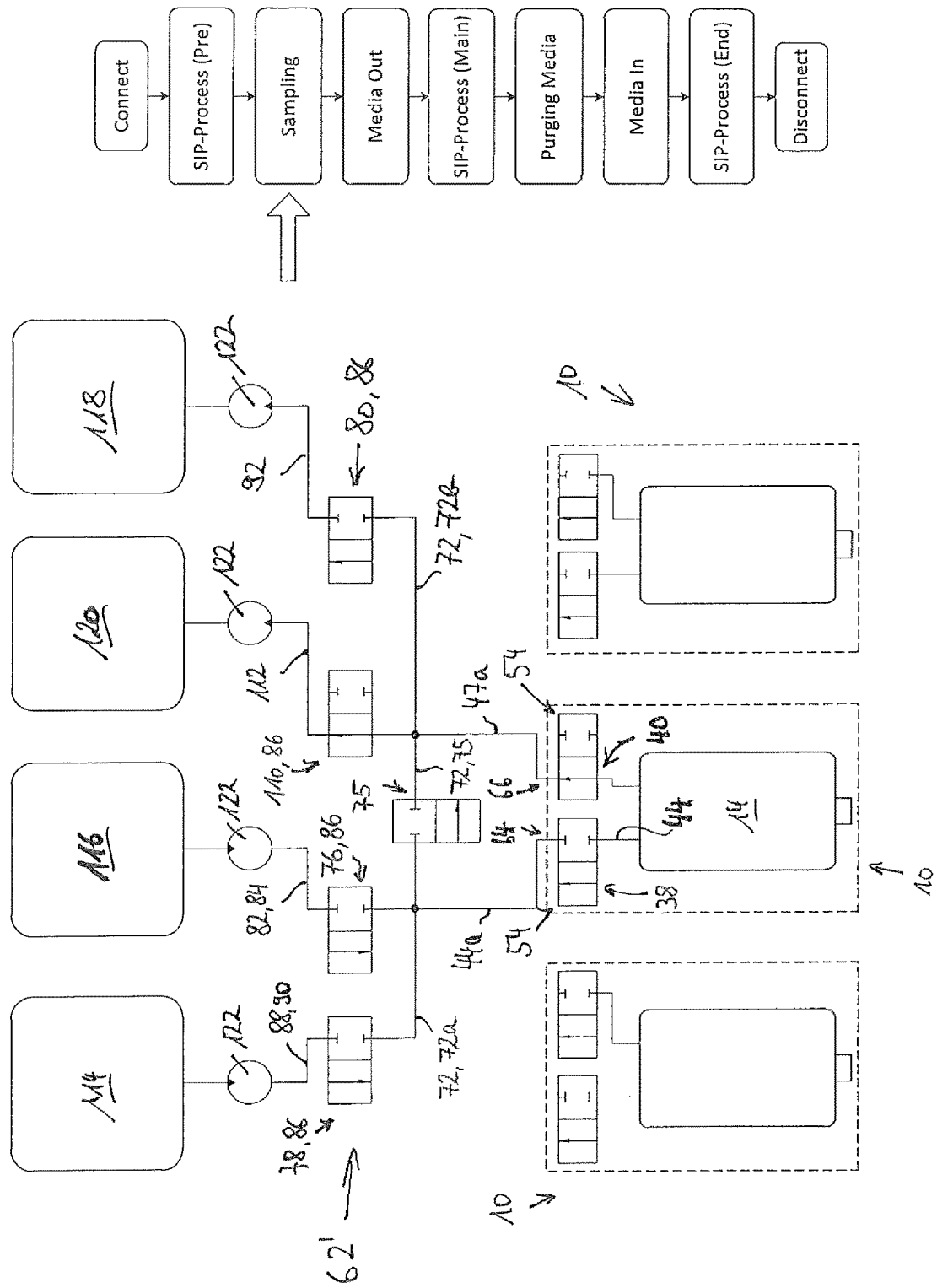

FIG. 8 shows random sampling following the previously discussed SIP cleaning process. The selection of the sequence of media removal from a cell culture container 10 before said media are introduced has the advantage that an introduction of nutrient medium into the cell culture container 10 does not take place until after an additional cleaning process, which further reduces the risk of cross-contamination due to contamination of a cell culture container 10 previously in coupling contact.

For random sample medium removal, the container valve configuration 38 of the first counter-coupling formation is switched to its outlet position. In addition, the valve configuration 86 of the fourth connection formation 110 is switched to its outlet position. All other valve configurations are in their blocked position. Thus, with the delivery pump 122 provided between the fourth connection formation 110 and the sampling container 120, a predetermined quantity of medium can be removed from the culture volume 14 of the coupled cell culture container 10 and placed into the sampling container 120. The separating valve configuration 74 in this case ensures that the sub-flow area 72a is not reached by the medium removed from the cell culture container 10.

Figure 9:
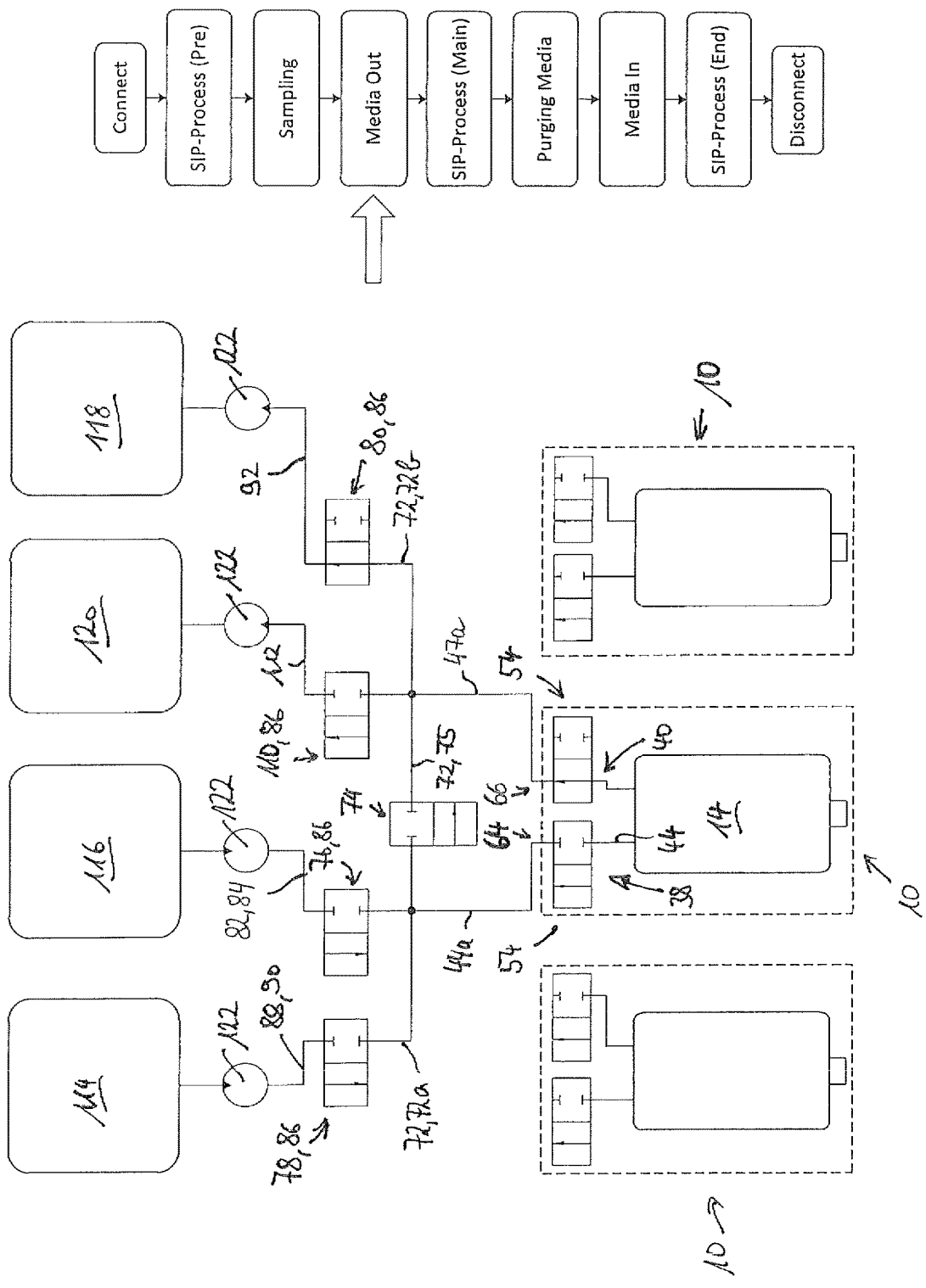

FIG. 9 shows a discharge, which is advantageously following the sampling, of used nutrient medium from the culture volume 14 of the coupled cell culture container 10. The sub-flow area 72b, which was already filled with the medium taken from the culture volume 14 in the previous sampling process step, has been filled again or remains filled with the same medium. However, contrary to the previous step, the used nutrient medium discharged through the second counter-coupling formation 40 is then conveyed through the valve configuration 86 of the third connection formation 80 by means of the delivery pump 122, connected directly thereto, in the disposal container 118. The remaining valve configurations 86 of the first, second, and fourth connection formation as well as the second container valve configuration 54 of the second counter-coupling formation 40 and the separating valve configuration 74 are in their blocked position in order to prevent any unnecessary wetting of flow paths caused by used nutrient medium.

Figure 10:
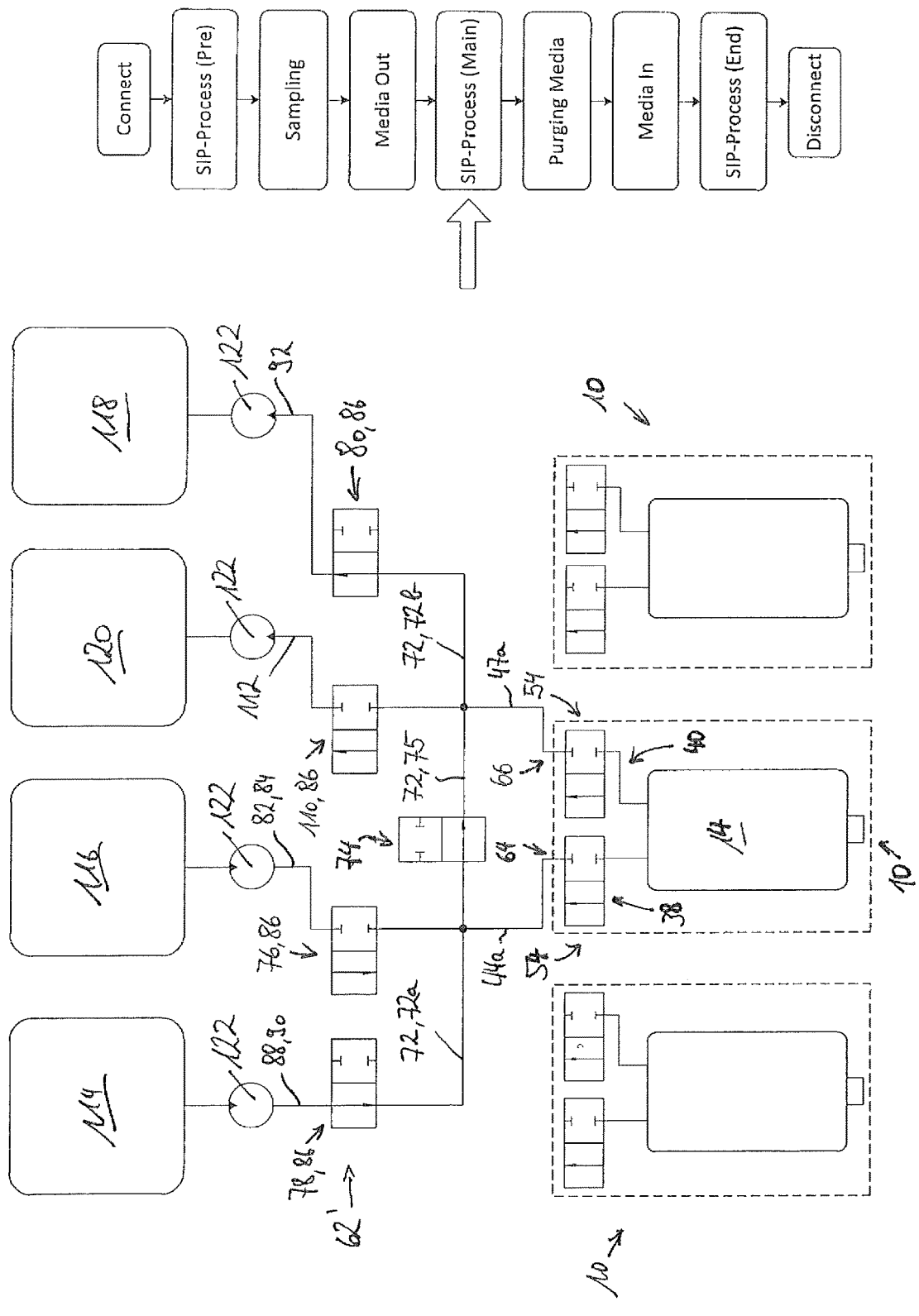

Before any filling of the cell culture container 10 with fresh nutrient medium takes place, there is another SIP cleaning process that takes place, which is shown in FIG. 10. The valve position configuration shown there corresponds precisely to that in FIG. 7, which serves the same purpose, and to the description thereof express reference is hereby made.

FIG. 11 shows how the liquid flow paths involved are flushed with fresh nutrient medium before the filling of the cell culture container 10 with fresh nutrient medium in order to remove any residue of cleaning fluid still remaining from the liquid supply interface 62'. To this end, both container valve configurations 54 are in the blocked position, as previously with the SIP cleaning process.

Of the valve configurations of the liquid supply interface 62', the valve configuration 86 of the first connection formation 76, the separating valve configuration 74, and the valve configuration 86 of the third connection formation are in their outlet position. All other valve configurations are in the blocked position. The delivery pumps 22 connected at the particular connection formations with open valve configurations ensure the passageway of fresh nutrient medium starting from the nutrient medium reservoir 116 into the disposal container 118.

FIG. 12 finally shows the process following the previously described flushing process of filling of the cell culture container 10 with fresh nutrient medium. To this end, the first container valve configuration 54 of the first counter-coupling formation 38 is adjusted in its outlet position, on one hand, while the second container valve configuration 54 of the second counter-coupling formation 40 is in its blocked position. All of the valve configurations on the liquid supply interface 62' side are in the blocked position with the exception of the valve configuration 86 of the first connection formation 76. Thus, fresh nutrient medium can be routed from the nutrient medium reservoir 116 through the first connection formation 76, the sub-flow area 72a, the first coupling flow path 44a, and the first counter-coupling formation 38, into the culture volume 14 of the cell culture container 10, by means of the delivery pump 122 connected to said first connection formation 76.

Therefore, only fresh nutrient medium or cleaning fluid always flows through the sub-flow area 72a. Used nutrient medium or cleaning fluid, on the other hand, only flows through the respective other sub-flow area 72b. The separation of the flow area 72 into the two sub-flow areas prevents used nutrient medium from a previously coupled cell culture container 10 that is still present in residue in a sub-flow area with fresh nutrient medium flowing through it from traveling from there into a subsequently coupled cell culture container 10. This shows the further reduction of the risk of cross-contamination.

A further SIP cleaning process, which is shown in FIG. 13, takes place before the attachment of the coupling contact with the still-coupled cell culture container 10, upon the filling of the coupled cell culture container 10 with fresh nutrient medium. The valve position configuration in this case corresponds to that of FIGS. 10 and 7, for understandable reasons, because it basically involves one and essentially the same cleaning process.

After a cleaning of the liquid supply interface 62' and the container valve configurations involved and the wettable points of the counter-coupling formations 38 and 40, there is a decoupling of the liquid supply interface 62' from the cell culture container 10, which has been coupled up to that point. This decoupling process is shown in FIG. 14.

FIGS. 15 to 18 show those processes of the method previously shown in FIGS. 6 to 14, which do not exclusively involve the flow of liquid from a reservoir into a container, 118 or 120, via the liquid connection interface, without liquid reaching a cell culture container or being removed from said container. Such process steps without changing the coupling or flow state at the coupling contact between the cell culture container and the liquid supply interface are all SIP cleaning steps (SIP process) as well as the flushing of the liquid supply interface with nutrient medium (purging media).

FIG. 15 shows the state of the cell culture system with alternative cell culture containers 10' and alternative liquid supply interface 62" directly after a liquid-transferring coupling contact has been established between the coupling formations of the liquid supply interface 62" and the cell culture container 10'.

The alternative cell culture container 10' of the cell culture system according to FIGS. 15 to 19 differs from the previously discussed cell culture container 10 only in that it has an additional third counter-coupling formation 40', in addition to the first counter-coupling formation 38 in the second counter-coupling formation 40.

Accordingly, the liquid supply interface 62" additionally has a third coupling formation 66' in addition to the first coupling formation 64 and the second coupling formation 66. The third coupling formation 66' and the third counter-coupling formation 40' may be advantageously formed like the first and the second coupling formation or counter-coupling formation, respectively, and do not differ from them except by the attachment location on the cell culture container 10' and at the liquid supply interface 62".

With the coupling process (connect) shown in FIG. 15, all container valve configurations 54 of the first to third counter-coupling formation are in the blocked position, for understandable reasons, in order to prevent uncontrolled escaping of liquid from the culture volume 14.

All valve configurations, 74 and 86, of the liquid supply interface 62" are also in their blocked position during the coupling process in FIG. 15 in order to prevent undesirable escaping of liquid from one of the reservoirs, 114 and 116, or the containers, 118 and 120. In addition, the pumps 122 are preferably switched off.

The SIP cleaning process following the coupling corresponds to that in FIG. 7 (see the previous description) with the proviso that all three container valve configurations 54 of the alternative cell culture container 10' are in the closed position.

FIG. 16 shows the taking of samples from the coupled alternative cell culture container 10'. The position of the valve configurations, 74 and 86, on the liquid supply interface side corresponds precisely to that in FIG. 8. This means the valve configuration 86 of the fourth connection formation is in the outlet position; all remaining valve configurations of the valve supply interface 62" are in their blocked position.

Because the alternative cell culture container 10' has three counter-coupling formations 38, 40, and 40', and preferably the first counter-coupling formation 38 is intended to be used for the infeed of fresh nutrient medium into the culture volume 14 in the preceding example, it is furthermore preferable for the second counter-coupling formation 42 to be provided exclusively for the discharge of used liquid from the culture volume 14 for the disposal, and the third counter-coupling formation 40' is exclusively allocated to a random sampling function with the container valve configuration 54 allocated to this and the delivery liquid flow path allocated to this. For this reason, only the third container valve configuration 54 of the third counter-coupling formation 40' is switched to its outlet position with the process shown in FIG. 16, while the remaining container valve configurations 54 of the cell culture container 10' are in their blocked position.

According to the above, with the disposal of used liquid from the culture volume 14 in the disposal container 118 shown in FIG. 17, only the second container valve configuration 54 of the second container counter-coupling formation of 40 is switched to its outlet position, while the first and the third container valve configuration of the first and the third counter-coupling formation, 38 and 40', respectively, are in their blocked position. The valve position configuration of the valve configurations 74 and 86 of the liquid supply interface 86 correspond to that in FIG. 9, to which description express reference is hereby made.

Upon the disposal of used liquid from the culture volume 14, particularly used nutrient medium, an SIP cleaning process occurs, which is not specifically outlined, as in the previous example. Because all container valve configurations 54 are in their blocked position in this process and the valve position configuration of the liquid supply interface 62" corresponds exactly to that in FIG. 10, express reference is made to the description in FIG. 10 for the following SIP cleaning process.

The same thing applies to the flushing process in which any cleaning fluid still remaining in the liquid supply interface is flushed out by a fresh nutrient medium. Express reference is made to the description of previous FIG. 11 for the process in the previous example, which is also not specifically outlined.

FIG. 18 shows the process of introducing fresh nutrient medium into the cell culture volume 14 of the alternative cell culture container 10'. The valve configurations, 74 and 86, on the liquid supply interface side correspond in their valve position configuration to that in FIG. 12, to which description express reference is hereby made in connection with the valve position of the valve arrangements on the liquid supply interface side and the corresponding pump operation.

On the cell culture container 10' side, only the first container valve configuration 54 of the first counter-coupling formation and 38 is in its outlet position; the two remaining container valve configurations are in their blocked position.

Regarding the subsequent SIP process step and the decoupling of the valve supplied interface 62" from the cell culture container 10', reference is made to the description in FIGS. 13 and 14, with the proviso that all three container valve configurations 54 of the cell culture container 10' are in the blocked position during these process steps. The valve position configuration of the valve configurations, 74 and 86, on the liquid supply interface side corresponds to that in FIGS. 13 and 14.

As a supplement to that, reference is made to the fact that not only the actually shown separating valve configuration 74 may be present at the alternative liquid supply interface 62", as shown in FIGS. 15 to 18, but there may be also a second separating supply interface 74', which is at the location indicated by the dashed line in FIG. 18. This second separating valve configuration 74' is always in its outlet position when an SIP cleaning step or a flushing step is implemented with fresh nutrient medium, that is when liquid is to be conveyed from a reservoir to the disposal container. In all remaining process steps, a second separating valve configuration 74' is also preferably in its blocked position.

FIGS. 19 to 21 shows the previously described cell culture system with a further modified cell culture container 10". Said cell culture container 10' has only one single counter-coupling formation 38. Accordingly, the further modified liquid supply interface 62m has only one single coupling formation 64. Because each flow to the cell culture container 10" and from it proceeds through one and the same coupling flow path 44a, a separating valve configuration may but does not have to be omitted. In the example shown in FIGS. 19 to 21, the separating valve configuration has been omitted. Otherwise, the liquid supply interface 62m corresponds to the previously described liquid supply interfaces, 62' and 62", regarding the connection formations and the valve configurations 86 provided there as well as the delivery pumps 122, reservoirs, 114 and 116, connected thereto, as well as containers, 118 and 120, the description of which is hereby referenced to explain the embodiment in FIGS. 19 to 21.

FIGS. 19, 20, and 21 only show those process steps of removing liquid from the cultural volume 14 and of filling the culture volume 14, in which actually liquid flows through the delivery liquid flow path 44 of the single counter-coupling formation 38. These are the process steps of random sampling (sampling, FIG. 19), media disposal (media out, FIG. 20), and the introduction of fresh nutrient medium into the culture volume 14 (media in, FIG. 21). In all remaining process steps, the single container valve configuration 54 of the single counter-coupling formation 38 is in its blocked position. The valve arrangements 86 of the liquid supply interface 62''' are in the same process steps (see the process sequence on the right-hand edge of FIGS. 6 to 21), each in the same position as the previously described modifications, 62' and 62". This also applies to the specifically shown process steps of random sampling (FIG. 19), media discharge from the cell culture container 10" (FIG. 20), and the introduction of fresh nutrient medium into the cell culture container 10" (FIG. 21). In this respect, the valve position configuration of the valve configurations 86 of the liquid supply interface 62''' in FIG. 19 correspond to that in FIG. 8 and FIG. 16, the valve configurations 86 in FIG. 20 correspond to that in FIGS. 9 and 17, and the valve position configuration of valve configurations 86 in FIG. 21 correspond to that in FIGS. 12 and 18. Regarding the description in FIGS. 19 to 21, express reference is made to the description of the extensively previously described figures.

Contrary to the previously described embodiments, fluid now flows continuously along one and the same delivery liquid flow path and coupling flow path, regardless of whether fresh nutrient medium is introduced into the cell culture container 10", removed from it for disposal, or removed from it for random sampling.

The invention claimed is:

1. A cell culture container for a cell culture system as well as for producible and detachable coupling contact with a liquid supply interface comprising:
 a container body enclosing a culture volume, said container body including a fill opening, through which gas, liquid, paste, and solid bodies can be filled into the container body and removed from said container body; and
 at least one counter-coupling formation formed separately from the fill opening, which is formed for establishing and detaching a coupling contact with a corresponding coupling formation of the liquid supply interface, wherein the at least one counter-coupling formation has a counter-coupling formation housing defining a delivery liquid flow path extending through the at least one counter-coupling formation and between an outer environment of the cell culture container and the culture volume, in order to introduce a liquid into the culture volume and/or to remove liquid from said culture volume via the delivery liquid flow path,
 wherein the at least one counter-coupling formation has a container valve configuration;
 wherein the container valve configuration can be switched, between a blocked position, in which the container valve configuration interrupts a liquid flow in the delivery liquid flow path, and an outlet position, in which the container valve configuration enables a liquid flow, by a control configuration with a signaling means generating an electric and/or magnetic and/or electromagnetic field, the field of which acts upon a correspondingly field-sensitive valve body of the container valve configuration without contact, said valve body being seated on a valve seat when the container valve configuration is in its blocked position, and being removed from the valve seat when the container valve configuration is in its outlet position.

2. The cell culture container according to claim 1, wherein the fill opening and the at least one separately formed counter-coupling formation are provided at opposite ends of the cell culture container.

3. The cell culture container according to claim 1, wherein the field generated by the signaling means is the magnetic field, and wherein the container valve configuration is pretensioned magnetically into the blocked position and adjustable into the outlet position by the magnetic field generated by the signaling means.

4. The cell culture container according to claim 3, wherein the container valve configuration has a permanently magnetic or a ferromagnetic tension component, such that an attracting magnetic tension force acts between the tension component and the valve body, which tensions the valve body for sealing contact with the valve seat.

5. A cell culture system comprising the cell culture container according to claim 1 and a liquid supply interface, wherein:
 the liquid supply interface comprises:
 a housing defining a flow area;
 a first connection formation for the liquid-transferring connection of a first fluid line to the housing;
 a second connection formation formed separately from the first connection formation and for the liquid-transferring connection of a second fluid line with the housing;
 a third connection formation formed separately from the first and second connection formations and for the liquid-transferring connection of the housing with a third fluid line;
 a coupling formation formed separately from the first, second and third connection formations, which is formed for the producible and detachable liquid-transferring coupling contact with the at least one corresponding counter-coupling formation of the cell culture container;
 a first liquid flow path, which extends between the flow area and the first connection formation for introducing a first liquid from outside into the flow area;
 a second liquid flow path, which extends between the flow area and the second connection formation for introducing a second liquid different from the first from the outside into the flow area;
 a third liquid flow path, which extends between the flow area and the third connection formation for removing a liquid from the flow area; and
 a coupling flow path, which extends between the flow area and the coupling formation in order to remove a liquid from the flow area and/or to introduce it to said flow area via the coupling formation,
 wherein:
 the first, the second, and the third liquid flow paths each have a valve configuration, which is completely surrounded, except for the respective liquid flow path, by the housing, incorporated in it, without a continuous signal- and/or power-transferring physical connection surrounded by the valve configuration up to the outside of the housing;
 a control configuration with a signaling means generating an electric and/or magnetic and/or electromagnetic field is assigned to each valve configuration, the field of which acts upon a valve body of the valve configuration without contact,
 each valve configuration can be switched off via the field, acting upon its valve body, between a blocked position, in which the valve configuration interrupts a liquid flow in the liquid flow path in which it is arranged, and an outlet position in which the valve configuration enables a liquid flow,
 the first connection formation connects the housing with a nutrient medium reservoir in a liquid-transferring manner and thus the first liquid flow path extends between the flow area and the nutrient medium reservoir;
 the second connection formation connects the housing with a cleaning fluid reservoir in a liquid-transferring manner and thus the second liquid flow path extends between the flow area and the cleaning fluid reservoir;
 the third connection formation connects the housing with a discharge in a liquid-transferring manner and thus the third liquid flow path extends between the flow area and the discharge;
 the coupling formation for coupling contact, which is producible and detachable in a liquid-transferring manner according to the operation, is formed with a counter-coupling formation of the cell culture container;
 the first liquid is a nutrient medium;
 the second liquid is a cleaning fluid; and the coupling flow path is formed in order to remove the nutrient medium from the flow area and supply it to the cell culture container and/or to remove it from said container and introduce it to the flow area via the coupling formation, in a state coupled with the at least one counter-coupling formation.

* * * * *